(12) United States Patent
Rairkar et al.

(10) Patent No.: US 8,337,815 B2
(45) Date of Patent: Dec. 25, 2012

(54) PULMONARY SURFACTANT FORMULATIONS

(75) Inventors: Maithili Rairkar, San Jose, CA (US); Rom E Eliaz, Sunnyvale, CA (US); Ralph Niven, Half Moon Bay, CA (US); Mark E. Johnson, Los Altos, CA (US)

(73) Assignee: Discovery Laboratories, Inc., Warrington, PA (US)

( * ) Notice: Subject to any disclaimer, the term of this patent is extended or adjusted under 35 U.S.C. 154(b) by 1087 days.

(21) Appl. No.: 11/316,308

(22) Filed: Dec. 21, 2005

(65) Prior Publication Data

US 2006/0286038 A1    Dec. 21, 2006

Related U.S. Application Data

(60) Provisional application No. 60/638,665, filed on Dec. 23, 2004.

(51) Int. Cl.
  *A61K 9/12* (2006.01)
  *A61K 38/00* (2006.01)
(52) U.S. Cl. .......................................... 424/45; 514/1.5
(58) Field of Classification Search .................... 424/45; 514/1.5
  See application file for complete search history.

(56) References Cited

U.S. PATENT DOCUMENTS

| | | | |
|---|---|---|---|
| 4,501,729 A | 2/1985 | Boucher et al. | 424/45 |
| 4,603,124 A | 7/1986 | Takei et al. | 514/78 |
| 4,828,844 A | 5/1989 | Rontgen-Odenthal | 424/489 |
| 4,895,719 A | 1/1990 | Radhakrishnan et al. | 424/45 |
| 5,013,720 A | 5/1991 | Whitsett | 514/12 |
| 5,024,995 A | 6/1991 | Robertson et al. | 514/21 |
| 5,164,369 A | 11/1992 | Cochrane et al. | 514/12 |
| 5,169,635 A | 12/1992 | Ono et al. | |
| 5,171,737 A | 12/1992 | Weiner et al. | 514/3 |
| 5,185,154 A | 2/1993 | Lasic et al. | 424/450 |
| 5,207,220 A | 5/1993 | Long | 128/207.14 |
| 5,238,920 A | 8/1993 | Sarin et al. | 514/12 |
| 5,260,273 A | 11/1993 | Cochrane et al. | 514/12 |
| 5,299,566 A | 4/1994 | Davis et al. | 128/200.24 |
| 5,302,581 A | 4/1994 | Sarin et al. | 514/12 |
| 5,309,903 A | 5/1994 | Long | 128/203.12 |
| 5,376,359 A | 12/1994 | Johnson | 424/46 |
| 5,407,914 A | 4/1995 | Cochrane et al. | 514/12 |
| 5,547,937 A | 8/1996 | Dhaon et al. | 514/12 |
| 5,552,161 A | 9/1996 | Disse et al. | 424/557 |
| 5,614,216 A | 3/1997 | Janoff | 424/450 |
| 5,674,860 A | 10/1997 | Carling et al. | 514/171 |
| 5,789,381 A | 8/1998 | Cochrane et al. | 514/13 |
| 5,874,064 A | 2/1999 | Edwards et al. | 424/46 |
| 5,934,273 A | 8/1999 | Andersson et al. | 128/203.12 |
| 5,952,303 A | 9/1999 | Bornstein et al. | 514/13 |
| 6,013,619 A | 1/2000 | Cochrane et al. | 514/2 |
| 6,013,764 A | 1/2000 | Abdel-Magid et al. | 530/327 |
| 6,116,237 A | 9/2000 | Schultz et al. | 128/203.15 |
| 6,120,795 A | 9/2000 | Klimchak et al. | 424/450 |
| 6,440,393 B1 | 8/2002 | Waldrep et al. | 424/45 |
| 6,613,734 B2 | 9/2003 | Cochrane et al. | 514/2 |
| 2002/0151597 A1 | 10/2002 | Banerjee et al. | 514/629 |

FOREIGN PATENT DOCUMENTS

| | | |
|---|---|---|
| WO | 89/06657 A1 | 7/1989 |
| WO | WO 90/07469 | 7/1990 |
| WO | 91/00871 A1 | 1/1991 |
| WO | 92/22315 A1 | 12/1992 |
| WO | 95/32992 A1 | 12/1995 |
| WO | 97/26863 A1 | 7/1997 |
| WO | 97/35882 A1 | 10/1997 |
| WO | 98/49191 A1 | 11/1998 |
| WO | WO 00/06198 | 2/2000 |
| WO | WO 00/47623 | 8/2000 |
| WO | WO 03/090682 | 11/2003 |

OTHER PUBLICATIONS

Quintero et al. Metabolism of phosphatidylglycerol by alveolar macrophages in vitro; Am. J. Physiol. Lung Cell Mol. Physiol. 279: pp. L399-L407, 2000.*

Yu et al., Lipid Compositional Analysis of Pulmonary Surfactant Monolayers and Monolayer-Associated Reservoirs; JLR Papers in Press. Published on Jan. 1, 2003 as Manuscript M200380-JLR200.*

Yu et al., Bovine Pulmonary Surfactant: Chemical Composition and Physical Properties; Lipids, vol. 18, No. 8, 1983.*

Orgeig et al. The roles of cholesterol in pulmonary surfactant: insights from comparative and evolutionary studies, Comparative Biochemistry and Physiology, Part A, vol. 129, pp. 75-89, 2001.*

Krol et al. Formation of Three-Dimensional Protein-Lipid Aggregates in Monolayer Films Induced by Surfactant Protein B; Biophysical Journal, vol. 79, pp. 904-918, Aug. 2000.*

Bell, D. et al., "Inflammatory response, neutrophil activation, and free radical production after acute myocardial infarction: effect of thrombolytic treatment," 1990, Br Heart J, 63, 82-87.

Borman, S., "Peptoids Eyed for Gene Therapy Applications," 1998, C & E News, 76, 56-57.

Cochrane, C. G. et al., "Pulmonary Surfactant Protein B (SP-B): Structure-Function Relationships," 1991, Science, 254, 566-568.

Cochrane, C. G. et al., "The efficacy and safety of KL4-surfactant in preterm infants with respiratory distress syndrome," 1996, Am J Resp & Crit Care Med, 153(1), 404-410.

Collaborative European Multicenter Study Group "Surfactant replacement therapy for severe neonatal respiratory distress syndrome: an international randomized clinical trial," Nov. 1988, Pediatrics 82(5), 683-691.

(Continued)

*Primary Examiner* — Benjamin Packard
*Assistant Examiner* — Adam C Milligan
(74) *Attorney, Agent, or Firm* — Potter Anderson & Corroon, LLP

(57) ABSTRACT

Synthetic pulmonary surfactant compositions comprising dipalmitoyl phosphatidylcholine, phosphatidylglycerol, and essentially neutral lipid, and having essentially no 1-palmitoyl 2-oleoyl phosphatidylglycerol and essentially no palmitic acid are provided. Methods for treating respiratory disease are also provided comprising administering a therapeutically effective amount of a synthetic pulmonary surfactant comprising dipalmitoyl phosphatidylcholine, phosphatidylglycerol, and essentially neutral lipid, and having essentially no 1-palmitoyl 2-oleoyl phosphatidylglycerol and essentially no palmitic acid.

20 Claims, 8 Drawing Sheets

OTHER PUBLICATIONS

Creuwels, L. A. J. M. et al., "The Pulmonary Surfactant System: Biochemical and Clinical Aspects," 1997, Lung, 175, 1-39.

Dakik, H. A. et al., "Repeated Doses of Tissue Plasminogen Activator for Failed Thrombolysis," 2001, Heart Dis, 3, 362-364.

Demling, R. H., "The Modern Version of Adult Respiratory Distress Syndrome," 1995, Annu Rev Med, 46, 193-202.

Desai S. R., "Acute Respiratory Distress Syndrome: Imaging of the Injured Lung," 2002, Clin Radiol, 57, 8-17.

Discher, B. M. et al., "Neutral Lipids Induce Critical Behavior in Interfacial Monolayers of Pulmonary Surfactant," 1999, Biochemistry, 38, 374-383.

Doring, G., "The Role of Neutrophil Elastase in Chronic Inflammation," 1994, Am J Respir Crit Care Med, 150, S114-S117.

Goldstein, I. M. et al., "Ceruloplasmin: An acute phase reactant that scavenges oxygen-derived free radicals," 1982, Ann N Y Acad Sci, 389, 368-379.

Gortner, I. et al., "A Multicenter Randomized Controlled Clinical Trial of Bovine Surfactant for Prevention of Respiratory Disease," 1990, Lung 168, (Suppl), 864-869.

Hallman, M. et al., "Evidence of Lung Surfactant Abnormality in Respiratory Failure," 1982, J Clin Inves, 70, 673-682.

Hansen, P. R., "Role of Neutrophils in Myocardial Ischemia and Reperfusion," 1995, Circulation, 91, 1872-1885.

Hart, D. A. et al., "Regulation of Plasminogen Activators and Their Inhibitors in Rheumatic Diseases: New Understanding and the Potential for New Directions," 1989, J Rheumatol, 16, 1184-1191.

Hybertson, B. M. et al., "Flow Injection Analysis of Nitrite Generated by Neutrophils and Endothelial Cells," 1994, Anal Lett, 27(15), 3081-3093.

Janoff, A., "Elastase in Tissue Injury," 1985, Annu Rev Med, 36, 207-216.

Kattwinkel, J., "Surfactant. Evolving Issues," 1998, Clinics in Perinatology, 25, 17-32.

Kehl, H. G. et al., "Left atrial thrombus in a 10-month-old boy—successful thrombolysis with recombinant tissue-type plasminogen activator after open-heart surgery: review of the literature," 1996, Intensive Care Med, 22, 968-971.

Kendig, J. W. et al., "A Comparison of Surfactant as Immediate Prophylaxis as Rescue Therapy in Newborns of Less Than 30 Weeks' Gestation," 1991, N. Engl. J. Med., 324(13), 865-871.

Kessel, et al., "Interactions of cholesterol with lipid bilayers: the preferred configuration and fluctuations," 2001, Biophys J., 81, 643-658.

King, R. J. et al., "Surface active materials from dog lung. II. Composition and physiological correlations," 1972, Am. J. Physiol., 223(3), 715-726.

Kruijtzer, J. A, "Synthesis in Solution of Peptoids using Fmoc-protected N-substituted Glycines,"1995, Tetrahedron Letters, 36(38), 6969-6972.

McLean, L. R. et al., "Minireview. Biomimetic Pulmonary Surfactants," 1995, Life Sciences, 56(6), 363-378.

McLoud, T., "Imaging Techniques for Diagnosis and Staging of Lung Cancer," 2002, Clin Chest Med, 23, 123-136.

McWilliams, A. et al., "Innovative molecular and imaging approaches for the detection of lung cancer and its precursor lesions," 2002, Oncogene, 21, 6949-6959.

Meienhofer, J., 1983, Hormonal Proteins and Peptides, vol. 2, pp. 46-267, Academic Press, New York.

Miller, S. M. et al., "Comparison of the Proteolytic Susceptibilities of Homologous L-Amino Acid, D-Amino Acid, and N-Substituted Glycine Peptide and Peptoid Oligomers," 1995, Drug Dev Res, 35, 20-32.

Morley, C. J. et al., "Dry Artificial Lung Surfactant and its Effect on Very Premature Babies," 1981, Lancet, 64-68.

Munkvad, S., "Fibrinolysis in patients with acute ischaemic heart disease," 1993, Dan Med Bull, 40, 383-408.

Notter, R. H. et al., "Pulmonary Surfactant: Physical Chemistry, Physiology, and Replacement," 1997, Reviews in Chemical Engineering, 13, 1-118.

Notter, R. H. et al., "Lung Surfactants for Replacement Therapy; Biochemical, Biophysical, and Clinical Aspects," 1987, Clin. Perinatol, 14(3), 433-479.

Phibbs, R. H. et al., "Initial Clinical Trial of EXOSURF, a Protein-Free Synthetic Surfactant, for the Prophylaxis and Early Treatment of Hyaline Membrane Disease," Jul. 1991, Pediatrics, 88, 1-9.

Radhakrishnan, A. et al., "Condensed Complexes of Cholesterol and Phospholipids," 1999, Biophys J., 77, 1507-1517.

Revak, S. D. et al., "Efficacy of synthetic peptide-containing surfactant in the treatment of respiratory distress syndrome in preterm infant rhesus monkeys," 1996, Ped. Res., 39(724), 715-724.

Riesenberg, K. et al., "Inhibition of superoxide production in human neutrophils by combinations of heparin and thrombolytic agents," 1995, Br Heart J, 73, 14-19.

Robertson, B., "Surfactant Substitution; Experimental Models and Clinical Applications,"1980, Lung, 158, 57-68.

Schroder and Kubke, 1965, the Peptides, vol. 1, Academic Press, New York.

Shore, P. A. et al., "A Method for the Fluorometric Assay of Histamine in Tissues," 1959, J Pharmacol Exp Ther, 127, 182-186.

Simon, R. J. et al., "Peptoids: A modular approach to drug discovery," 1992, Proc. Natl. Acad. Sci. U.S.A., 89, 9367-9371.

Stewart and Young, 1969, Solid Phase Peptide Synthesis, W. H. Freeman Co., San Francisco, 1969.

Vincent, J. S. et al., "Raman spectroscopic studies of model human pulmonary surfactant systems: phospholipid interactions with peptide paradigms for the surfactant protein SP-B," 1991, Biochemistry, 30, 8395-8401.

Weissmann, G. et al., "Neutrophils: release of mediators of inflammation with special reference to rheumatoid arthritis," 1982, Ann N Y Acad Sci, 389, 11-24.

Zivkovic, I. et al., "7-Chloro-3-methyl-3-4-dihydro-2H-1,2,4 benzothiadiazine S,S-dioxide (IDRA 21): a benzothiadiazine derivative that enhances cognition by attenuating DL-alpha-amino-2,3-dihydro-5-methyl-3-oxo-4-isoxazolepropanoic acid (AMPA) receptor desensitization," 1995, J Pharmacol Exp Ther, 272, 300-309.

Zuckermann, R. N. et al., "Efficient Method for the Preparation of Peptoids [Oligo(N-substituted glucines)] by Submonomer Sold-Phase Synthesis," 1992, J. Am. Chem. Soc., 114, 10646-10647.

Baeumner, A., et al., "Liposome-based Immunosensors: 1. Influence of Hapten Spacer Length . . . ", Analytical Letters, 29(15), 2601-2613 (1996), XP009069996 ISSN: 0003-2719.

Fleming, B. D., et al., "Surface Respreading After Collapse of Monolayers . . . ", Chemistry and Physics of Lipids, 49(1-2), 81-86 (1988), XP009070005 ISSN: 0009-3084.

Samuni, A. M., et al., "Gamma-irradiation Damage to Liposomes Differing . . . ", Free Radical Biol. & Medicine, 23(7), 972-979 (1997), XP002391866 ISSN: 0891-5849.

Yu, Shou-Hwa., et al., "Lipid Compositional Analysis of Pulmonary Surfactant Monolayers and . . . ", J. of Lipid Research, 44(3), 621-629 (2003), XP002391865 ISSN: 0022-2275.

International Preliminary Report on Patentability, issued Jun. 27, 2007 in Application No. PCT/US2005/046862, filed Dec. 22, 2005.

International Search Report, issued Sep. 19, 2006 in PCT/US2005/046862, filed Dec. 22, 2005.

* cited by examiner

PULMONARY SURFACTANT FORMULATIONS

CROSS-REFERENCE TO RELATED APPLICATIONS

This application claims priority, under 35 U.S.C. §119(e), to application Ser. No. 60/638,665 filed Dec. 23, 2004, the disclosure of which is incorporated by reference in its entirety.

FIELD

The invention relates to a novel lung surfactant composition comprising a pulmonary surfactant and a neutral lipid that exhibits a reduction in surface tension, low viscosity characteristics and enhanced storage stability.

BACKGROUND

Pulmonary surfactants are complex lipid and protein compositions that can be extracted from animals, purified and used to treat neonatal respiratory distress syndrome. Animal-derived surfactants are difficult to purify, limited by the scale to which they can be manufactured and have the potential to cause immunogenic reactions on repeat use, and thus are not indicated for use in other clinical indications. To capitalize on the potential use of surfactants in a range of pulmonary disease states requires the availability of a functional surfactant that can both be manufactured at the scale required and which inherently has the flexibility to be modified for use with specific delivery systems and for specific disease states. One such surfactant under development is synthetically produced and has a composition of dipalmitoyl phosphatidylcholine (DPPC), or 1-palmitoyl 2-oleoyl phosphatidylglycerol (POPG), palmitic acid (PA) and an engineered mimic of surfactant protein B, called sinapultide (KL4 or $KL_4$) dispersed within an isotonic aqueous Tris-saline buffer of pH 7.7. The composition is currently under evaluation for use in RDS, meconium aspiration syndrome and in acute respiratory distress syndrome at various concentrations. The composition can also be modified for use by reducing, increasing or substituting one or more of the components.

Previous work has shown that formulations having reduced concentrations of either palmitic acid (PA) or cetyl alcohol (CA), relative to that of 30 mg/ml Surfaxin® (i.e., 4.05 mg/ml PA), exhibit lower viscosity when compared side by side with Surfaxin®. However, this is at the expense of loss of functional surface tension activity as the content of the palmitic acid or cetyl alcohol is reduced as measured by in vitro techniques. However, by using DPPG instead of POPG and adding cholesterol, palmitic acid could be completely omitted from the formulation with the resulting compositions exhibiting low viscosity while retaining good surface activity.

Recently it was found that cholesterol at low concentrations contribute significantly to the termination of phase separation during compression of interfacial films of the pulmonary surfactant (Discher et al., 1999, Biochemistry 38:374-83). Other studies suggested that at low concentration cholesterol contributes to the elastic response of the neighboring lipids in the lipid bilayer. This elastic response is expressed by a tendency of the surrounding lipids to adapt to the hydrophobic shape of cholesterol (Kessel et al., 2001, Biophys J. 81:643-58). In fact, cholesterol can modulate physical properties of lipid bilayers to induce liquid phase coexistence and corresponding domain formation (Radhakrishnan and McConnell, 1999, Biophys J. 77:1507-17).

Due to these findings, and the existence of cholesterol in natural lung surfactant this report is related to the inclusion of various concentrations of cholesterol, 1-30 mol %, focusing on 2-15 mol %, to $KL_4$-containing formulations to improve their properties. In particular (but not limited to) it can help in aerosolization of $KL_4$-containing formulations by decreasing the viscosity of the formulations and otherwise modifying the structure of the concentrated lipid-based dispersions, such that an increase in the amount of surfactant that can be aerosolized is achieved. In addition, inclusion of cholesterol with saturated lipids in the surfactant formulation could facilitate and enhance an increase in lateral stability of the monolayer essential for alveolar expansion. Moreover, since the transition temperature of DPPC is close to body temperature (41° C.) cholesterol will "soften" the bilayer, increase its permeability and eliminate phase-separation during alveolar compression and expansion. Furthermore, cholesterol will contribute to membrane perturbation effects, thus will decrease the energy of interfacial tension and lower line tension (as in the critical point, when the characteristics of two phases become similar). Similarly it may improve lipid-peptide interaction, particularly $KL_4$-DPPC/DPPG interactions.

The current standard method of delivery does not instantaneously deliver the surfactant over the surface of the airways and alveoli. The procedure involves the introduction of a bolus of surfactant to a patient who has been intubated (an invasive procedure). In order to distribute throughout the lungs, the surfactant must be aspirated deeper into the lungs during breathing maneuvers while simultaneously flowing and spreading across the lung surfaces. Accordingly, a formulation that can be effectively delivered as an aerosol in sufficient quantity and of appropriate aerosol size and size characteristics should distribute throughout the lungs and exert a therapeutic response without the need to employ an invasive delivery procedure.

BRIEF SUMMARY

The present invention is related to novel lung surfactant compositions and methods of use related thereto. The invention relates, in part, to the discovery that formulations containing a surfactant, 1,2 dipalmitoyl phosphatidylcholine (DPPC), phosphatidylglycerol (DPPG), essentially neutral lipid, and essentially no palmitic acid (PA) or 1-palmitoyl 2-oleoyl phosphatidylglycerol (POPG) exhibit higher aerosol output rates from various aerosol generators and low viscosity compared to formulations containing PA and/or POPG. Thus, the present invention relates to a pulmonary surfactant comprising dipalmitoyl phosphatidylcholine, phosphatidylglycerol, and essentially neutral lipid, and having essentially no 1-palmitoyl 2-oleoyl phosphatidylglycerol and essentially no palmitic acid.

The present invention also provides a synthetic pulmonary surfactant comprising dipalmitoyl phosphatidylcholine, phosphatidylglycerol, and essentially neutral lipid, and having essentially no 1-palmitoyl 2-oleoyl phosphatidylglycerol and essentially no palmitic acid. In some aspects, the phosphatidylglycerol is saturated, non-saturated or semi-saturated. In some such aspects, the pulmonary surfactant the saturated phosphatidylglycerol is dipalmitoyl phosphatidylglycerol. In some aspects, the pulmonary surfactant each of 1-palmitoyl 2-oleoyl phosphatidylglycerol and palmitic acid are present in an amount less than about five mole percent of total phospholipid. In some aspects, the essentially neutral lipid comprises cholesterol. In other aspects, the pulmonary surfactant the essentially neutral lipid comprises a fatty acid, a fatty acid ester, a fatty acid alcohol, cholesterol, corticosteroid, glucocorticosteroid, trifluorinate glucocorticoid, β2 agonist, plant sterol, phospholipid, phosphatidylcholine, phosphatidyl ethanolamine, phosphatidylinositol, sphingomyelin, diglycerides, diolein, dipalmitolein, mixed caprylin-caprin, triglycerides, triolein, tripalmitolein, trilinolein, tricaprylin, or trilaurin. In some such aspects, the cholesterol concentration is from about 0.1 mol % to about 50 mol %. In some such aspects, the cholesterol concentration is from about 1 mol % to about 20 mol %. In some such aspects, the cholesterol concentration is cholesterol concentration from about 8 mol % to about 15 mol %. In some such aspects, the molar ratio of dipalmitoyl phosphatidylcholine to dipalmitoyl phosphatidylglycerol is 4 to 1. In some such aspects, the molar ratio of dipalmitoyl phosphatidylcholine to dipalmitoyl phosphatidylglycerol is 7 to 3. In some such aspects, the molar ratio of dipalmitoyl phosphatidylcholine to dipalmitoyl phosphatidylglycerol is 3 to 1. In some such aspects, the total concentration of dipalmitoyl phosphatidylcholine and phosphatidylglycerol is from about 10 mg/ml to about 150 mg/ml. In some aspects, the total concentration of dipalmitoyl phosphatidylcholine and phosphatidylglycerol is from about 50 mg/ml to about 125 mg/ml. In other aspects, a dynamic surface tension of the surfactant as measured by pulsating bubble surface tensionometry is about 10 mN or less. In some such aspects, the pulmonary surfactant further comprises a surfactant polypeptide. In certain aspects, the surfactant polypeptide comprises at least 10 amino acid residues and no more than about 60 amino acid residues, the polypeptide including a sequence having alternating hydrophobic and hydrophilic amino acid residue regions represented by the formula (Za Ub)c Zd, wherein: Z is a hydrophilic amino acid residue independently selected from the group consisting of R and K; U is a hydrophobic amino acid residue independently selected from the group consisting of L and C; a is 1 or 2; b has an average value of about 3 to about 8; c is 1 to 10; and d is 0 to 2. In some such aspects, the pulmonary surfactant has an amino acid residue sequence represented by the formula: KLLLLKLLLLKLLLLKLLLLK (SEQ ID NO:1).

The present invention also provides a synthetic pulmonary surfactant consisting essentially of dipalmitoyl phosphatidylcholine, non-saturated phosphatidylglycerol, essentially neutral lipid and surfactant polypeptide. In some aspects, the non-saturated phosphatidylglycerol is palmitoyl oleyl phosphatidylglycerol. In some such aspects, the essentially neutral lipid is cholesterol. In some such aspects, the surfactant polypeptide has an amino acid residue sequence represented by the formula: KLLLLKLLLLKLLLLKLLLLK (SEQ ID NO:1).

The present invention provides a synthetic pulmonary surfactant consisting essentially of dipalmitoyl phosphatidylcholine, nonsaturated phosphatidylglycerol, palmitic acid, essentially neutral lipid and surfactant polypeptide. In some such aspects, the nonsaturated phosphatidylglycerol is palmitoyl oleyl phosphatidylglycerol. In some such aspects, the neutral lipid is cholesterol. In some such aspects, the surfactant polypeptide has an amino acid residue sequence represented by the formula: KLLLLKLLLLKLLLLKLLLLK (SEQ ID NO:1).

The present invention also provides a synthetic pulmonary surfactant consisting essentially of dipalmitoyl phosphatidylcholine, dipalmitoyl phosphatidylglycerol, essentially neutral lipid and surfactant polypeptide. In some such aspects, the essentially neutral lipid is cholesterol. In some such aspects, the essentially neutral lipid comprises a fatty acid, a fatty acid ester, a fatty acid alcohol, cholesterol, corticosteroid, glucocorticosteroid, trifluorinate glucocorticoid, β2 agonist, plant sterol, phospholipid, phosphatidylcholine, phosphatidylethanolamine, phosphatidylinositol, sphingomyelin, diglycerides, fatty alcohols, diolein, dipalmitolein, mixed caprylin-caprin, triglycerides, triolein, tripalmitolein, trilinolein, tricaprylin, or trilaurin. In some such aspects, the surfactant polypeptide comprises at least 10 amino acid residues and no more than about 60 amino acid residues, the polypeptide including a sequence having alternating hydrophobic and hydrophilic amino acid residue regions represented by the formula (Za Ub)c Zd, wherein: Z is a hydrophilic amino acid residue independently selected from the group consisting of R and K; U is a hydrophobic amino acid residue independently selected from the group consisting of L and C; a is 1 or 2; b has an average value of about 3 to about 8; c is 1 to 10; and d is 0 to 2. In some such methods, the pulmonary surfactant has an amino acid residue sequence represented by the formula: KLLLLKLLLLKLLLLKLLLLK (SEQ ID NO:1).

The present invention provides a synthetic pulmonary surfactant consisting of dipalmitoyl phosphatidylcholine, dipalmitoyl phosphatidylglycerol, and essentially neutral lipid. In some aspects, the essentially neutral lipid comprises cholesterol. In some such aspects, the essentially neutral lipid comprises a fatty acid, a fatty acid ester, a fatty acid alcohol, cholesterol, corticosteroid, glucocorticosteroid, trifluorinate glucocorticoid, β2 agonist, plant sterol, phospholipid, phosphatidylcholine, phosphatidyl ethanolamine, phosphatidylinositol, sphingomyelin, diglycerides, diolein, dipalmitolein, mixed caprylin-caprin, triglycerides, triolein, tripalmitolein, trilinolein, tricaprylin, or trilaurin.

The present invention further provides methods of treating respiratory disease, such as infant respiratory distress syndrome, comprising administering a therapeutically effective amount of a synthetic pulmonary surfactant comprising dipalmitoyl phosphatidylcholine, phosphatidylglycerol, and essentially neutral lipid, and having essentially no 1-palmitoyl 2-oleoyl phosphatidylglycerol and essentially no palmitic acid. In some such methods, the phosphatidylglycerol is saturated, non-saturated or semi-saturated. In some such methods, the saturated phosphatidylglycerol is dipalmitoyl phosphatidylglycerol. In other methods, the essentially neutral lipid comprises cholesterol. In some methods, the essentially neutral lipid comprises a fatty acid, a fatty acid ester, a fatty acid alcohol, cholesterol, corticosteroid, plant sterol, phospholipid, phosphatidylcholine, phosphatidyl ethanolamine, phosphatidylinositol, sphingomyelin, diglycerides, diolein, dipalmitolein, mixed caprylin-caprin, triglycerides, triolein, tripalmitolein, trilinolein, tricaprylin, or trilaurin.

The present invention further provides methods of treating respiratory disease, such as infant respiratory distress syndrome, comprising administering a therapeutically effective amount of a synthetic pulmonary surfactant, the surfactant consisting essentially of dipalmitoyl phosphatidylcholine, phosphatidylglycerol, essentially neutral lipid and a surfactant polypeptide, the polypeptide having alternating hydrophobic and hydrophilic amino acid residue regions, represented by the formula (Za Ub)c Zd, wherein: Z is a hydrophilic amino acid residue independently selected from the group consisting of R and K; U is a hydrophobic amino acid residue independently selected from the group consisting of L and C; a is 1 or 2; b has an average value of about 3 to about 8; c is 1 to 10; and d is 0 to 2. In some such methods, the phosphatidylglycerol is saturated, non-saturated or semi-saturated. In some such methods, the saturated phosphatidylglycerol is dipalmitoyl phosphatidylglycerol. In some such methods, the essentially neutral lipid comprises cholesterol. In some such methods, the polypeptide has an amino acid residue sequence represented by the formula: KLLLLKLLLLKLLLLKLLLLK (SEQ ID NO:11.

The present invention further provides methods of treating respiratory disease, such as respiratory distress syndrome, comprising administering a therapeutically effective amount of a synthetic pulmonary surfactant comprising dipalmitoyl phosphatidylcholine, dipalmitoyl phosphatidylglycerol, and essentially neutral lipid, and having essentially no 1-palmitoyl 2-oleoyl phosphatidylglycerol and essentially no palmitic acid.

The present invention further provides methods of treating respiratory disease, such as respiratory distress syndrome, comprising administering a therapeutically effective amount of a synthetic pulmonary surfactant, the surfactant comprising one or more pharmaceutically acceptable phospholipids admixed with a polypeptide having alternating hydrophobic and hydrophilic amino acid residue regions, represented by the formula (Za Ub)c Zd, wherein: Z is a hydrophilic amino acid residue independently selected from the group consisting of R and K; U is a hydrophobic amino acid residue independently selected from the group consisting of L and C; a is 1 or 2; b has an average value of about 3 to about 8; c is 1 to 10; and d is 0 to 2. In some such methods, the polypeptide has an amino acid residue sequence represented by the formula: KLLLLKLLLLKLLLLKLLLLK (SEQ ID NO:1).

The present invention also provides a method of manufacturing a synthetic pulmonary surfactant comprising terminally sterilizing the surfactant of the present invention by autoclaving.

The present invention further provides a method for drug delivery to the pulmonary system comprising administering to a patient in need of treatment an effective amount of a synthetic pulmonary surfactant of the present invention, wherein the microparticles have a diameter between 0.5 microns and 5 microns and viscosity less than 30 cP at a cholesterol concentration from about 8 mole % to about 15 mole %, in a pharmaceutically acceptable carrier for administration to the lungs.

The present invention further provides a method for reducing viscosity of a drug delivery formulation to the pulmonary system comprising adding cholesterol at a concentration from about 8 mol % to about 15 mol % to the synthetic pulmonary surfactant of the present invention as described above.

The present invention further provides a method for increasing the aerosolization rate of a drug delivery formulation to the pulmonary system comprising adding cholesterol at a concentration from about 8 mol % to about 15 mol % to the synthetic pulmonary surfactant of the present invention as described above.

The present invention further provides a method for increasing storage stability of a drug delivery formulation to the pulmonary system comprising adding cholesterol at a concentration from about 8 mol % to about 15 mol % to the synthetic pulmonary surfactant of claim 1 as described above.

BRIEF DESCRIPTION OF THE DRAWINGS

FIG. 5. Aerosol output rate of formulations measured at 60 mg/ml (mg-TPL/min)

DETAILED DESCRIPTION

A. General Overview

Figure 1:
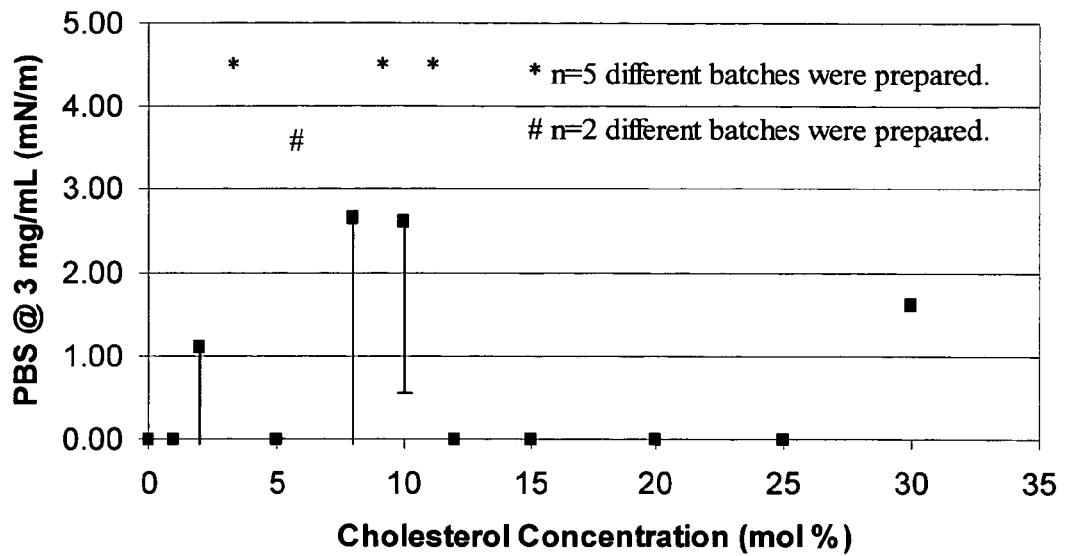
FIG. 1. Surface activities of DPPG formulations measured at 3 mg/ml TPL

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

The present invention delivers mixtures of active agents in a media. As used herein the term "mixture" means a solution, suspension, dispersion or emulsion. "Emulsion" refers to a mixture of two or more generally immiscible liquids, and is generally in the form of a colloid. The mixture can be of lipids, for example, which can be homogeneously or heterogeneously dispersed throughout the emulsion. Alternatively, the lipids can be aggregated in the form of, for example, clusters or layers, including monolayers or bilayers. "Suspension" or "dispersion" refers to a mixture, preferably finely divided, of two or more phases (solid, liquid or gas), such as, for example liquid in liquid, solid in solid, gas in liquid, and the like which preferably can remain stable for extended periods of time. Preferably the dispersion of this invention is a fluid dispersion.

The mixture comprises the active agent at desired concentration and a medium. Preferably, the concentration of the active agent in the medium is selected to ensure that the patient is receiving an effective amount of active agent and is typically about 1 to about 100/mg/ml. Based on the active agent chosen and the medium, one of skill in the art is readily able to determine the proper concentration. Mixtures often include one or more wetting agents. The term "wetting agent" means a material that reduces the surface tension of a liquid and therefore increases its adhesion to a solid surface. Preferably, a wetting agent comprises a molecule with a hydrophilic group at one end and a hydrophobic group at the other. The hydrophilic group is believed to prevent beading or collection of a material on a surface, such as the nasal prongs. Suitable wetting agents are soaps, alcohols, fatty acids, combinations thereof and the like.

"Composition" and "formulation" are used interchangeably to refer to a product which results by combining or mixing more than one element or ingredient.

"Storage stability" refers to the stability of a drug product under the anticipated storage conditions. A formulation with enhanced or improved storage stability would exhibit less chemical degradation and less changes in key physical properties (e.g., loss in in vitro surface activity in the case of lung surfactants) during storage and over time.

"Active agent" as used herein refers to a substance or combination of substances that can be used for therapeutic purposes (e.g., a drug), diagnostic purposes or prophylactic purposes via pulmonary delivery. For example, an active agent can be useful for diagnosing the presence or absence of a disease or a condition in a patient and/or for the treatment of a disease or condition in a patient. "Active agent" thus refers to substances or combinations of substances that are capable of exerting a biological effect when delivered by pulmonary routes. The bioactive agents can be neutral, positively or negatively charged. Exemplary agents include, for example, insulins, autocoids, antimicrobials, antipyretics, anti-inflammatories, surfactants, antibodies, antifungals, antibacterials, analgesics, anorectics, antiarthritics, antispasmodics, antidepressants, antipsychotics, antiepileptics, antimalarials, antiprotozoals, anti-gout agents, tranquilizers, anxiolytics, narcotic antagonists, antiparkinsonisms, cholinergic agonists, antithyroid agents, antioxidants, antineoplastics, antivirals, appetite suppressants, antiemetics, anticholinergics, antihistaminics, antimigraines, bone modulating agents, bronchodilators and anti-asthma drugs, chelators, antidotes and antagonists, contrast media, corticosteroids, mucolytics, cough suppressants and nasal decongestants, lipid regulating drugs, general anesthetics, local anesthetics, muscle relaxants, nutritional agents, parasympathomimetics, prostaglandins, radiopharmaceuticals, diuretics, antiarrhythmics, antiemetics, immunomodulators, hematopoietics, anticoagulants and thrombolytics, coronary, cerebral or peripheral vasodilators, hormones, contraceptives, diuretics, antihypertensives, cardiovascular agents such as cardiotonic agents, narcotics, vitamins, vaccines, and the like.

Preferably, the active agent is a high-dose therapeutic. Such high dose therapeutics include antibiotics, such as amikacin, gentamicin, colistin, tobramycin, amphotericin B. Others include mucolytic agents such as N-acetylcysteine, Nacystelyn, alginase, mercaptoethanol and the like. Antiviral agents such as ribavirin, gancyclovir, and the like, diamidines such as pentamidine and the like and proteins such as antibodies are also contemplated.

Currently, at least three classes of lung surfactant replacements for the treatment of respiratory diseases are contemplated: (1) "natural"; (2) "synthetic"; and "biomimetic". Natural surfactant replacements are prepared from animal lungs by lavage or extraction with organic solvents, and purified by chromatography (see, e.g., Creuwels et al., 1997 *Lung* 175: 1-39; Notter and Wang, 1997, *Reviews in Chemical Engineering* 13:1-118; and Kattwinkel, 1998, *Clinics in Perinatology* 25:17-32). A number of animal-derived surfactant replacements are FDA-approved (see, e.g., Kattwinkel, 1998, *Clinics in Perinatology* 25:17-32; Gortner, 1990, *Lung* 168 (Suppl):864-869; Kendig et al., 1991, N. Engl. J. Med. 324: 865-871; Collaborative European Multicenter Study Group. Surfactant replacement therapy in severe neonatal respiratory distress syndrome: An international randomized clinical trial. 1988 *Pediatrics* 82:683-691. Synthetic surfactant replacements are by definition protein-free, and are made from synthetic phospholipids with added chemical agents (lipids or detergents) to facilitate adsorption and spreading (see, e.g., Morley et al., 1981 Lancet i:64-68 and Phibbs. et al., 1991, *Pediatrics* 88:1-9). A third class of formulations is the "biomimetic lung surfactants." Biomimetic surfactants are designed to mimic the biophysical characteristics of natural lung surfactant while not sharing its precise molecular composition. These formulations contain synthetic phospholipid mixtures in combination with recombinantly-derived or chemically-synthesized peptide analogs to SP-B and/or SP-C (for a review of biomimetic surfactants, see, e.g., McLean and Lewis, 1995, *Life Sciences* 56:363-378). All three classes of surfactants are contemplated for use in the formulations of the present invention, unless otherwise noted. Therefore "surfactant" as used herein includes natural, synthetic and biomimetic surfactants.

The preferred active agent is a substance or combination of substances that is used for pulmonary prophylactic or rescue therapy, such as a surfactant. A particularly preferred surfactant is "$KL_4$" (also referred to as "$KL_4$ surfactant" which incorporates a peptide mimetic of surfactant protein B (see WO 89/06657; WO 92/22315; WO 98/49191; U.S. Pat. Nos. 5,260,273; 5,164,369; 5,407,914; 5,789,381; 5,952,303; 6,013,619; 6,013,764; 6,120,795; and 6,613,734; all of which are expressly incorporated by reference in their entirety for all purposes). $KL_4$ is based on Surfaxin® and preferably is present in the instant invention as an aqueous dispersion of dipalmitoyl phosphatidylcholine, phosphatidylglycerol, and essentially neutral lipid (e.g., cholesterol), and having essentially no 1-palmitoyl 2-oleoyl phosphatidylglycerol and essentially no palmitic acid. Such surfactant peptides are cationic peptides that can be derived from animal sources or can be derived synthetically as discussed above. When an animal-derived surfactant is employed, the surfactant is often bovine or porcine-derived.

Preferably the peptide is present within an aqueous dispersion of phospholipids and free fatty acids or fatty alcohols, in this case 1,2 dipalmitoyl phosphatidylcholine (DPPC), phosphatidylglycerol (DPPG), and cholesterol, and essentially no palmitic acid (PA) or 1-palmitoyl 2-oleoyl phosphatidylglycerol (POPG).

This invention contemplates the use of other cationic peptides beyond $KL_4$ surfactant. Preferably, cationic peptides consist of at least about 10, preferably at least 11 amino acid residues, and no more than about 60, more usually fewer than about 35 and preferably fewer than about 25 amino acid residues.

Many cationic peptides have been disclosed in the art. See, for example, U.S. Pat. No. 5,164,369, which is hereby incorporated by reference in its entirety for all purposes. Examples of cationic peptides include KLLLLKLLLLKLLLLK (SEQ ID NO:1) (KL$_4$), DLLLLDLLLLDLLLLDLLLLD (SEQ ID NO:4) (DL4), RLLLLRLLLLRLLLLRLLLLR (SEQ ID NO:5) (RL4), RLLLLLLLLRLLLLLLLLRLL (SEQ ID NO:6) (RL8), RRLLLLLLLRRLLLLLLLRRL (SEQ ID NO:7) (R2L7), RLLLLCLLLRLLLLLCLLLR (SEQ ID NO:12), RLLLLLCLLLRLLLLCLLLRLL (SEQ ID NO:13), and RLLLLCLLLRLLLLCLLLRLLLLCLLL-RDLLLDLLLDLLLDLLLDLLLD (SEQ ID NO:14), and polylysine, magainans, defensins, polymyxins, iseganan, histatin and the like. Preferably, the cationic peptide is KL$_4$.

"Surfactant activity" for a protein or polypeptide is defined as the ability, when combined with lipids, either alone or in combination with other proteins, to exhibit activity in the in vivo assay of Robertson 1980, *Lung* 158:57-68. In this assay, the sample to be assessed is administered through an endotracheal tube to fetal rabbits or lambs delivered prematurely by Caesarian section. (These "preemies" lack their own PS, and are supported on a ventilator.) Measurements of lung compliance, blood gases and ventilator pressure provide indices of activity. Preliminary assessment of activity may also be made by an in vitro assay, for example that of King and Clements, 1972, *Am. J. Physiol.* 223:715-726, or that illustrated below which utilizes a measurement of surface tension at a air-water interface when a protein or polypeptide is admixed with a phospholipid and a neutral lipid.

Examples of phospholipids useful in surfactant compositions include native and/or synthetic phospholipids. Phospholipids that can be used include phosphatidylcholines, phospatidylglycerols, phosphatidylethanolamines, phosphatidylserines, phosphatidic acids, and phosphatidylethanolamines. Exemplary phospholipids include 1,2 dipalmitoyl phosphatidylcholine (DPPC), phosphatidylglycerol (DPPG), dilauryl phosphatidylcholine (DLPC) (C12:0), dimyristoyl phosphatidylcholine (DMPC) (C14:0), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2), dipalmitoyl phosphatidylethanolamine (DPPE), dioleoylphosphatidylethanolamine (DOPE), dioleoyl phosphatidylglycerol (DOPG), palmitoyloleoyl phosphatidylglycerol (POPG), distearoylphosphatidylserine (DSPS) soybean lecithin, egg yolk lecithin, sphingomyelin, phosphatidylinositols, diphosphatidylglycerol, phosphatidylethanolamine, and phosphatidic acids, Egg phosphatidylcholine (EPC).

In one preferred embodiment, the phospholipids useful in surfactant compositions of the invention include 1,2 dipalmitoyl phosphatidylcholine (DPPC) and phosphatidylglycerol and essentially no palmitoyloleoyl phosphatidylglycerol (POPG). In another preferred embodiment, the phosphatidylglycerol is saturated, non-saturated or semi-saturated. In another preferred embodiment, the saturated phosphatidylglycerol is dipalmitoyl phosphatidylglycerol (DPPG).

Examples of neutral lipids useful in surfactant compositions of the invention include native and/or synthetic neutral lipids. Neutral lipids can include a fatty acid, a fatty acid ester, a fatty acid alcohol, cholesterol, corticosteroid, glucocorticosteroid, trifluorinate glucocorticoid, β2 agonist, plant sterol, phospholipid, phosphatidylcholine, phosphatidyl ethanolamine, phosphatidylinositol, sphingomyelin, diglycerides, diolein, dipalmitolein, mixed caprylin-caprin, triglycerides, triolein, tripalmitolein, trilinolein, tricaprylin, or trilaurin. In a preferred embodiment, the essentially neutral lipid is cholesterol.

Examples of fatty acids, fatty acid esters and fatty acid alcohols useful in surfactant compositions include methyl palmitate, cholesteryl palmitate and the like, palmitic acid, cetyl alcohol, lauric acid, myristic acid, stearic acid, phytanic acid, dipalmitic acid, and the like. In a preferred embodiment, the surfactant comprises essentially no palmitic acid.

The term "medium" refers to both aqueous and non-aqueous mediums. The preferred medium is chosen so as not cause any adverse effect on the biological activity of the active agent being delivered.

Preferably, the non-aqueous mediums can include, for example, hydrogen-containing chlorofluorocarbons, fluorocarbons certain organic compounds and admixtures thereof. To provide some adjunctive respiratory support, and to provide efficient lung filling in the degassed state, the perfluorocarbon liquid should have an oxygen solubility greater than about 40 ml/100 ml. Representative perfluorocarbon liquids include, but are note limited to, FC-84, FC-72, RM-82, FC-75 (3M Company, Minneapolis, Minn.), RM-101 (MDI Corporation, Bridgeport, Conn.), dimethyladamantane (Sun Tech, Inc.), trimethylbicyclononane (Sun Tech, Inc.), and perfluorodecalin (Green Cross Corp., Japan), combinations thereof and the like.

Preferably, when an aqueous medium is employed, the medium is a water-containing liquid. Suitable mediums include isotonic ionic solutions preferably buffered to within 1 pH unit of physiologic pH (7.3). The medium should be free of pathogens and other deleterious materials and can be composed of pure water but also optionally can include up to about 20% by volume and preferably up to about 5% of nontoxic organic liquids such as oxy-group containing liquids such as alcohols, esters, ethers, ketones and the like. In selecting organic components it is important to avoid materials which are likely to give rise to undesired reactions such as intoxication, sedation, and the like. Preferably, the medium is saline or tromethamine buffer.

"Respiratory" refers to the process by which oxygen is taken into the body and carbon dioxide is discharged, through the bodily system including the nose, throat, larynx, trachea, bronchi and lungs.

"Respiratory disease", "respiratory disorder", "respiratory condition", and "respiratory syndrome" refer to any one of several ailments that involve inflammation and affect a component of the respiratory system including especially the trachea, bronchi and lungs. Examples of such ailments include acute alveolar disease, obstructive respiratory disease (e.g., asthma; bronchitis; and chronic obstructive pulmonary disease, referred to as COPD), upper airway disease (e.g., such as otitis media, rhinitis/sinusitis and sleep apnea), insterstitial lung disease, allergy, and respiratory infection (e.g., pneumonia, pneyumocystis carinii, and respiratory syncitial virus (RSV)).

Specific examples of acute alveolar disease include acute lung injury (ALI), acute respiratory distress syndrome (ARDS), meconium aspiration syndrome (MAS) and respiratory distress syndrome (RDS). ALI is associated with conditions that either directly or indirectly injure the air sacs of the lung, the alveoli. ALI is a syndrome of inflammation and increased permeability of the lungs with an associated breakdown of the lungs' surfactant layer. The most serious manifestation of ALI is ARDS. Among the causes of ALI are complications typically associated with certain major surgeries, mechanical ventilator induced lung injury (often referred to as VILI), smoke inhalation, pneumonia, and sepsis.

ARDS in adults is a life-threatening disorder for which no approved therapies exist anywhere in the world. It is characterized by an excess of fluid in the lungs and decreased oxygen levels in the patient. One prominent characteristic of this disorder is the destruction of surfactants naturally present in lung tissue. The conditions are caused by illnesses including pneumonia and septic shock (a toxic condition caused by infection) and events such as smoke inhalation, near drowning, industrial accidents and other traumas.

MAS in full term infants is a condition in which full-term infants are born with meconium in their lungs that depletes the natural surfactant in their lungs. Meconium is an infant's first bowel movement in its mother's womb and when inhaled, MAS can occur. MAS can be life-threatening as a result of the failure of the lungs.

RDS in premature infants is a condition in which premature infants are born with an insufficient amount of their own natural surfactant. Premature infants born prior to 32 weeks gestation have not fully developed a natural lung surfactant and therefore need treatment to sustain life. This condition often results in the need for mechanical ventilation.

COPD is an umbrella term as used herein to describe lung disease associated with airflow obstruction. Most generally, emphysema, chronic bronchitis and chronic asthma either alone or in combinations fall into this category.

Asthma is a common disease characterized by sudden constriction and inflammation of the lungs. Constriction of the upper airway system occurs when the airway muscles tighten, while inflammation is a swelling of the airways usually due to an allergic reaction caused by an airborne irritant. Both of these events cause airways to narrow and can result in wheezing, shortness of breath and chest tightness. Several studies have shown that surfactant damage and dysfunction is a significant component of asthma. Airway constriction occurs when there is a surfactant dysfunction in the airways of the deep lung of the type that develops during an asthma attack.

In addition, the compositions and methods of the present invention are useful in the treatment of other respiratory diseases and disorders, such acute bronchitis, bronchiectasis, pneumonia (including ventilator-associated pneumonia, nosocomial pneumonia, viral pneumonia, bacterial pneumonia, mycobacterial pneumonia, fungal pneumonia, eosinophilic pneumonia, and Pneumocystis carinii pneumonia), tuberculosis, cystic fibrosis (CF), emphysema radiation pneumonitis, inflammation caused by smoking, pulmonary edema, pneumoconiosis, sarcoidiosis, silicosis, asbestosis, berylliosis, coal worker's pneumonoconiosis (CWP), byssinosis, interstitial lung diseases (ILD) such as idiopathic pulmonary fibrosis, ILD associated with collagen vascular disorders, systemic lupus erythematosus, rheumatoid arthritis, ankylosing spondylitis, systemic sclerosis, and pulmonary inflammation that is a result of or is secondary to another disorder such as influenza.

"Inflammation" or "inflammatory response" refer to an innate immune response that occurs when tissues are injured by bacteria, trauma, toxins, heat, or any other cause. The damaged tissue releases compounds including histamine, bradykinin, and serotonin. Inflammation refers to both acute responses (i.e., responses in which the inflammatory processes are active) and chronic responses (i.e., responses marked by slow progression and formation of new connective tissue). Acute and chronic inflammation can be distinguished by the cell types involved. Acute inflammation often involves polymorphonuclear neutrophils; whereas chronic inflammation is normally characterized by a lymphohistiocytic and/or granulomatous response. Inflammation includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils. Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids can be referred to herein by either their commonly known three letter symbols or by the one-letter symbols recommended by the IUPAC-IUB Biochemical Nomenclature Commission (see Table 1 below). Nucleotides, likewise, can be referred to by their commonly accepted single-letter codes.

TABLE 1

| BOL 1-Letter | 3-Letter | AMINO ACID |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | He | L-isoleuine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a radical such as H and OH (hydrogen and hydroxyl) at the amino- and carboxy-termini, respectively, or a further sequence of one or more amino acid residues.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Such salts also include acid addition salts formed with inorganic acids (e.g. hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., C1-6 alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

"Pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

Except when noted, "subject" or "patient" are used interchangeably and refer to mammals such as human patients and non-human primates, as well as experimental animals such as rabbits, dogs, cats, rats, mice, and other animals. Accordingly, "subject" or "patient" as used herein means any mammalian patient or subject to which the compositions of the invention can be administered. In some embodiments of the present invention, the patient will be suffering from a condition that causes a respiratory disease or condition, e.g., ARDS or RDS. In an exemplary embodiment of the present invention, to identify subject patients for treatment with a pharmaceutical composition comprising one or more surfactant compositions according to the methods of the invention, accepted screening methods are employed to determine the status of an existing disease or condition in a subject or risk factors associated with a targeted or suspected disease or condition. These screening methods include, for example, examinations to determine whether a subject is suffering from a respiratory disease. These and other routine methods allow the clinician to select subjects in need of therapy.

"Treating" refers to any indicia of success in the treatment or amelioration or prevention of, for example, a respiratory disease such as ARDS or RDS, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination. Accordingly, the term "treating" includes the administration of the compounds or agents of the present invention to prevent or delay, to alleviate, or to arrest or inhibit development of the symptoms or conditions associated with respiratory disease.

"Therapeutic effect" refers to the reduction, elimination, or prevention of the disease, symptoms of the disease, or side effects of the disease in the subject. A "therapeutically effective amount" means the amount that, when administered to a subject for treating a disease, condition or disorder, is sufficient to effect treatment for that disease.

"Therapeutic compound" as used herein refers to a compound useful in the prophylaxis or treatment of a respiratory disease or condition.

"Therapeutically effective" as used herein refers to a characteristic of an amount of a therapeutic compound, or a characteristic of amounts of combined therapeutic compounds in combination therapy. The amount or combined amounts achieve the goal of preventing, avoiding, reducing or eliminating the respiratory disease or condition.

"Pro-drug" refers to a compound that is a drug precursor which, following administration to a subject and subsequent absorption, is converted to an active species in vivo via some process, such as a metabolic process. Other products from the conversion process are easily disposed of by the body. The more preferred pro-drugs are those involving a conversion process that produces products that are generally accepted as safe.

"Concomitant administration", "concurrent administration", or "co-administration" as used herein includes administration of the active agents (e.g., the $KL_4$ composition), in conjunction or combination, together, or before or after each other. The multiple agent(s) may be administered by the same or by different routes, simultaneously or sequentially, as long as they are given in a manner sufficient to allow all agents to achieve effective concentrations at the site of action. A person of ordinary skill in the art, would have no difficulty determining the appropriate timing, sequence and dosages of administration for particular drugs and compositions of the present invention.

B. Pulmonary Surfactants—Overview

Naturally-occurring pulmonary surfactant is a complex mixture of lipids and proteins that promotes the formation of a monolayer at the alveolar air-water interface and, by reducing the surface tension and stabilizing the monolayer to withstand high surface pressures generated during compression, prevents collapse of the alveolus during expiration. Premature infants, and occasionally full term neonates, can lack sufficient endogenous surfactant, or lack a fully functional surfactant for normal lung function. This can give rise to a condition termed respiratory distress syndrome (RDS) which can necessitate mechanical ventilation and administration of hyperbaric oxygen. Such intervention, unfortunately, can produce permanent damage to lung tissue and can cause retinopathy of prematurity (ROP) leading to blindness.

Pulmonary surfactant (PS) lines the alveolar epithelium of mature mammalian lungs. Natural PS has been described as a "lipoprotein complex" because it contains both phospholipids and apoproteins that interact to reduce surface tension at the lung air-liquid interface. Natural surfactant contains several lipid species of which dipalmitoyl phosphatidylcholine (DPPC) is the major component together with phosphatidylglycerol (PG) and palmitic acid (PA). At least four specific proteins are associated, termed SP-A, SP-B, SP-C and SP-D. Of these four, SP-B and SP-C are distinct, low molecular weight, relatively hydrophobic proteins that have been shown to enhance the surface-active properties of surfactant phospholipid mixtures. It is believed that they facilitate transfer of lipids from the bulk phase lamellar organization to the air-water interface and also stabilize the lipid monolayer during expiration. The structure of SP-B (which is alternatively referred to as SP18) is unusual in that charged amino acids (predominantly basic) are located at fairly regular intervals within stretches of otherwise hydrophobic residues. For the domain consisting of residues 59-80 of the native SP-B sequence, these charged groups have been shown to be necessary for biological activity. In addition, natural and synthetic peptides which are modeled on this hydrophobic-hydrophilic domain when combined with DPPC and PG, exhibit good surfactant activity.

Surfactant is stored in lung epithelial cells in the form of lamellar bodies and, following export, it undergoes a structural transition to form tubular myelin before giving rise to a monolayer at the air-water interface. It has been proposed that surfactant proteins SP-A, -B and -C can facilitate these structural transitions and stabilize the lipid monolayer during expansion and contraction of the alveolus; however, an understanding of lipid-protein interactions at the molecular level is presently lacking. The present invention, therefore, has important implications not only with respect to the treatment of RDS in infants as well as adults, but also because of the insight it can provide into lipid-protein interactions in general.

Several exogenous surfactant formulations are currently used in the treatment of infant RDS. While these have reduced morbidity and mortality, continual improvements are needed. In particular, because of the complications that can arise due to mechanical ventilation and administration of hyperbaric oxygen, the sooner normal lung function can be established in a premature infant the more favorable will be the clinical outcome.

Consistent with the foregoing, important characteristics in an exogenous surfactant include the ability to spread rapidly to the alveoli following administration and the ability to maintain a stable monolayer at the alveolar air-water interface so that repeated treatment is not required. Thus, various compounds and compositions that are useful in the preparation of superior exogenous surfactants are disclosed herein.

C. Surfactant Compositions

A surfactant composition of the present invention can contain any of a variety of pharmaceutically acceptable compounds having surfactant activity to form a pulmonary surfactant (PS) useful in the treatment of respiratory distress syndrome. Typically a surfactant composition has admixed therein one or more phospholipids. Phospholipids useful in forming alveolar surfactants are well known in the art. See Notter, R. H. and D. L. Shapiro, 1987, *Clin. Perinatol* 14:433-79, for a review of the use of both native and synthetic phospholipids for surfactants.

The surfactant compositions of this invention that are prepared using a protein, a polypeptide, an amino acid residue-containing molecule, or another organic molecule of the present invention having surfactant activity (collectively, "surfactant molecules"), that can include one or more phospholipids and neutral lipids, are well suited for the treatment of respiratory diseases such as RDS and ARDS. Such surfactant compositions typically range from dilute to concentrated, depending upon the intended use as described further herein.

Thus a surfactant composition can contain from as little as about 0.05 to almost 100 weight percent lipid, so long as the resulting composition has surfactant activity. By weight percent is meant the percentage of a compound by weight in a composition by weight. Thus, a composition having 50 weight percent lipid contains, for example, 50 grams lipid per 100 grams total composition. Typically, a surfactant composition contains 0.1 to 50 weight percent lipid, although higher concentrations of lipid can be used for "bolus" methods and for preparing more dilute surfactant compositions from a concentrated stock.

Exemplary surfactant compositions containing phospholipid and a surfactant molecule can contain, therefore, 0.1, 1, 10, 50, 80, to almost 100 weight percent lipid and about 50, 20, 10, to less than 1 weight percent surfactant molecule. Similarly, exemplary surfactant compositions containing neutral lipid and a surfactant molecule can contain, therefore 0.1, 1, 10, 50, 80, to almost 100 weight percent lipid and about 50, 20, 10, to less than 1 weight percent surfactant molecule The surfactant composition is prepared by admixing a solution of a surfactant molecule with a dispersion of lipid components, or by admixing the surfactant molecule with a dispersion of lipids, or by admixing the surfactant molecule and phospholipids directly in the presence of organic solvent.

Lipid-based surfactant compositions of the present invention are generally sterile colloidal dispersions containing a surfactant molecule of the present invention that has been combined with the lipids and a free fatty acid, alcohol or neutral lipid in an organic solvent system, dried, and then rehydrated. Because of the large variety of compounds and substances that have surfactant activity, it is to be understood that a surfactant composition useful in the present invention can be free from detectable protein or polypeptide, and contains only phospholipids, aqueous medium and/or buffers. In various preferred embodiments of the present invention, pulmonary surfactants that are effective in treating respiratory diseases, such as RDS or ARDS, comprising an effective amount of a surfactant molecule admixed with a pharmaceutically acceptable phospholipids and neutral lipid are disclosed. In one preferred embodiment, the surfactant molecule is a polypeptide or protein; in other preferred embodiments, the surfactant molecule is an organic molecule displaying surfactant activity which can comprise amino acid residues, modified amino acids, amino acid derivatives, amino acid analogs, and the like molecules, or other organic molecules mimicking that activity.

Methods for determining the optimal polypeptide:lipid weight ratios for a given polypeptide-phospholipid-neutral lipid combination are well known. Therapeutically effective ratios are in the range of about 1:5 to about 1:10,000, preferably about 1:7 to about 1:5,000, more preferably about 1:10 to about 1:1000, and more preferably about 1:15 to about 1:100. The lipid portion of a surfactant composition of the present invention is preferably about 50 to about 90, more preferably about 50 to about 75, weight percent dipalmitoylphosphatidylcholine (DPPC) with the remainder comprising, phosphatidylglycerol (PG), essentially neutral lipid or admixtures thereof.

Phospholipids useful in forming the present surfactant compositions are well known in the art. (See, e.g., Notter, R. H. and D. L. Shapiro 1988, for a review of the use of both native and synthetic phospholipids for surfactants). Methods and materials useful in the preparation of preferred surfactant compositions as disclosed herein are also described in the Examples that follow. See also WO 89/06657; WO 92/22315; WO 98/49191; U.S. Pat. Nos. 5,260,273; 5,164,369; 5,407,914; 5,789,381; 5,952,303; 6,013,619; 6,013,764; 6,120,795; and 6,613,734.

A pulmonary surfactant of the present invention is generally prepared by admixing a solution of a subject polypeptide with a suspension of liposomes or by admixing the subject polypeptide (or other organic surfactant molecule) and lipids directly in the presence of organic solvent. The solvent is then removed by dialysis or evaporation under nitrogen and/or exposure to vacuum or by other appropriate techniques.

A pulmonary surfactant composition is preferably formulated for endotracheal administration, e.g., typically as a liquid suspension, as a dry powder "dust", or as an aerosol. Those of skill in the art will appreciate that surfactant compositions of the present invention can be formulated for a variety of uses and methods of administration including, without limitation, liquid suspensions or aerosols which can be used for lavage.

For example, a surfactant (surfactant molecule-lipid micelle) can be suspended in a liquid with a pharmaceutically acceptable excipient such as water, saline, dextrose, glycerol and the like. A surfactant-containing therapeutic composition can also contain small amounts of non-toxic auxiliary substances such as pH buffering agents, including tromethamine acetate (TRIS acetate), sodium acetate, sodium phosphate, and the like. To prepare a surfactant in dust form, a surfactant is prepared as described herein, then lyophilized and recovered as a dry powder. Surfactants can be prepared by processes known per se and familiar to the person skilled in the art, for example as described in WO95/32992. Lyophilized preparations are disclosed, for example, in WO 97/35882, WO 91/00871 and DE 3229179. WO 97/26863 describes a process for the preparation of powdered pulmonary surfactant formulations by spray drying. Other approaches such as supercritical fluid extraction can also be envisioned as means to produce dry powders.

If it is to be used in aerosol administration, a subject surfactant is supplied in finely divided form along with an additional surfactant and propellant. Typical surfactants which can be administered are phospholipids and esters. However, it is preferred, in the present case, to utilize the other components of the surfactant complex, DPPC and PG together with essentially neutral lipid. Useful propellants are typically gases at ambient conditions, and are condensed under pressure. Lower alkane and fluorinated alkane, such as Freon, can be used. The aerosol is packaged in a container equipped with a suitable valve so that the ingredients can be maintained under pressure until released.

To prepare a surfactant composition, the surfactant molecule or polypeptide molecule is dissolved in an organic solvent that maintains the molecule in its monomeric, substantially aggregate-free form. Preferred such solvents can be polar or non-polar and exhibit solubility parameter delta (δ) values in the range of about 9 to about 15 $(cal \cdot cm^3)^{1/2}$ or about 9 Hildebrand units (H) to about 15H.

Particularly preferred solvents are the hydrogen bonded solvents such as the $C_1$ to $C_4$ alipathic alcohols, i.e., methanol (δ=14.5H), ethanol (δ=12.7H), n-propanol (δ=11.9H), isopropanol (δ=11.5H), n-butanol (δ=11.4H), iso-butanol (δ=10.8H) and t-butanol (?). Among halogenated solvents particularly preferred are trifluoroethanol (TFE) and chloroform (δ=9.3H). Mixtures or blends of aliphatic alcohols and halogenated solvents can be utilized as well. In a preferred method for producing a surfactant composition, the polypeptide or other surfactant molecule is dissolved in the organic solvent together with the phospholipids, and the resulting solution is combined with an aqueous buffer solution. The resulting dispersion is then dialyzed or evaporated to remove the organic solvent leaving an aqueous dispersion. Alternatively, the organic and aqueous solvent components can be removed by evaporation and vacuum. The dried, or partially dried lipid/polypeptide mixture thus produced is rehydrated in an aqueous buffer system to produce the surfactant dispersion.

The present invention also contemplates a variety of surfactant compositions, particularly lipid-based surfactants. Thus, in one preferred embodiment, the invention discloses a lipid-based surfactant composition prepared from a polypeptide comprising about 10 amino acid residues and no more than about 60 amino acid residues and is constituted by alternating groupings of charged amino acid residues and uncharged amino acid residues, and a pharmaceutically acceptable phospholipid, wherein the polypeptide is present in an amount sufficient to increase the surfactant activity of the composition above that of the phospholipid.

In another preferred variation, a surfactant composition of the present invention comprises a surfactant molecule constituted by alternating groupings of charged and uncharged residues; the residues can be amino acids, modified amino acids, amino acid analogs or derivatives, and the like. Molecules having surfactant activity as disclosed herein are especially preferred for use in compositions of the present invention.

In various preferred embodiments of the present invention, as noted previously, surfactant compositions also comprise one or more phospholipids. The polypeptide:lipid weight ratio is in the range of about 1:7 to about 1:1,000 in various preferred surfactant compositions of the present invention. Suitable phospholipids are preferably selected from the following group: 1,2-dipalmitoyl-sn-glycero-3-phosphocholine (dipalmitoylphosphatidylcholine, DPPC); phosphatidyl glycerol (PG); and an admixture of DPPC and PG in a weight ratio of about 3:1.

The surfactant compositions of the present invention can have essentially no 1-palmitoyl 2-oleoyl phosphatidylglycerol and no palmitic acid, in various preferred embodiments.

In one preferred embodiment, the phospholipids useful in surfactant compositions of the invention include 1,2 dipalmitoyl phosphatidylcholine (DPPC) and phosphatidylglycerol and essentially no palmitoyloleoyl phosphatidylglycerol (POPG). In another preferred embodiment, the phosphatidylglycerol is saturated, non-saturated or semi-saturated. In another preferred embodiment, the saturated phosphatidylglycerol is dipalmitoyl phosphatidylglycerol (DPPG). If an admixture of DPPC and PG is selected, it is preferable that DPPC and PG be present in a weight ratio of preferably about 4:1; more preferably about 7:3; and most preferably 3:1.

For example, in one embodiment of the present invention, a 30 mg/ml surfactant composition of the present invention comprises, in each ml of composition, 0.801 mg $KL_4$ peptide, 22.5 mg DPPC, 7.5 mg DPPG, 1.575 mg cholesterol, and essentially no PA or POPG. In various embodiments, the surfactant is prepared aseptically and is supplied in vials containing a sufficient volume to deliver either various volumes of the dispersion.

Thus, in one exemplary formulation, a preparation having a phospholipid concentration of about 30 mg/mL administered at a dosage volume of about 5 mL/kg would result in a dose of about 150 mg/kg. Similarly, an exemplary preparation having a lipid concentration of about 60 mg/mL administered at a dosage volume of about 5 mL/kg would result in a dose of about 300 mg/kg.

One preferred final surfactant composition comprises a sterile colloidal dispersion containing surfactant polypeptide (or other surfactant molecules according to the present invention). By way of illustration, a drug product/surfactant composition containing $KL_4$ peptide is described as exemplary.

Peptide is preferably combined with lipids in an organic solvent system which is then added to an aqueous buffer system or vice a versa. The organic solvent is removed from the resulting aqueous-organic mixture by thin film evaporation allowing the colloidal dispersion to form. All processing is performed aseptically.

One exemplary composition comprises surfactant peptide and a lipid component. In one embodiment, the lipid component comprises 1,2 dipalmitoyl phosphatidylcholine (DPPC) and phosphatidylglycerol, essentially neutral lipid, and having essentially no palmitoyloleoyl phosphatidylglycerol (POPG). In another preferred embodiment, the phosphatidylglycerol is saturated, non-saturated or semi-saturated. In another preferred embodiment, the saturated phosphatidylglycerol is dipalmitoyl phosphatidylglycerol (DPPG).

For example, a surfactant composition including $KL_4$ peptide can be prepared from an admixture of DPPC and PG in a 3:1 ratio by weight with cholesterol, 5.25% by weight compared with the phospholipids, in an organic solvent. $KL_4$ peptide is prepared in the surfactant dispersion as 2.7% by weight of the phospholipid concentration. Organic solvents can be removed from the lipid/peptide mixture by evaporation under nitrogen and vacuum or related means. A Tris buffer solution can be added to form colloidal dispersions of the peptide-containing surfactant.

A Tham buffer system can also be included in a surfactant composition of the present invention. (Tham is a buffering agent also known as Tris, tromethamine, and tris(hydroxymethyl)aminomethane.) In various preferred embodiments, the compositions have a pH range of about 6.5-8.0.

A wide variety of surfactant molecules, proteins, and polypeptides which are preferred for use according to the disclosed methods are described above and in the sections that follow. Other preferred components of surfactant compositions used as disclosed herein include a variety of phospholipids and neutral lipid as further described herein.

For example, currently there are a variety of known surfactants described that have been used in related methods. These surfactants are all suitable for use in the present invention according to the discovery that dilute surfactant lavages are beneficial. These surfactants include natural surfactants derived from aqueous lavages of lungs of mammals, including but not limited to bovine, porcine or ovine species, such as BLES, Infasurf or CLSE (Calf Lung Surfactant, Forest Products), Alveofact (Thomae, Germany); surfactant material extracted from animal lungs by, but not limited to, organic solvents, such as Surfactant TA (Tokyo Tanabe, Japan), Survanta (Beractant, Abbott Laboratories, Abbott Park, Ill.), Curosurf (Chiesi Farmaceutici, Parma, Italy). Surfactants can comprise mixtures of phospholipids, spreading agents and proteins or peptides. The phospholipids can be phosphatidyl choline (e.g., DPPC) and phosphatidylglycerol (e.g., DPPG). The spreading agents increase the rate of spreading along an air-water interface and can include cholesterol, detergents and the like. The proteins and peptides can be any of those described herein or which otherwise augment surfactant activity of phospholipids, and can be isolated from natural sources, synthesized chemically or produced by recombinant DNA methodologies, such as SP-C.

Details regarding the composition and methods of preparation of these and other surfactants can be found in the following U.S. Pat. Nos. 4,603,124, 5,013,720, 5,024,995, 5,171,737, 5,185,154, 5,238,920, 5,302,581, 5,547,937, 5,552,161, and 5,614,216, the disclosures of which are hereby incorporated by reference.

A surfactant of the present invention is administered, as appropriate to the dosage form, by endotracheal tube, by bronchoscope, by cannula, by spray administration, or by aerosolization (atomization, nebulization, dispersion and deaggregation) of the suspension or dust into the inspired gas. Amounts of PS between about 1.0 and about 500 mg/kg, and preferably about 50 mg to about 500 mg/kg, and typically a dose of about 50 mg/kg, 100 mg/kg, 133 mg/kg, or 200 mg/kg, measured in terms of total phospholipid content, are administered in one dose. For use in newly born infants, one or two administrations are generally sufficient. For adults, sufficient reconstituted surfactant complex is preferably administered to produce a $PO_2$ within the normal range (see, e.g., Hallman et al., 1982, *J Clin Inves* 70:673-682). It must be appreciated that the treatment regimen can vary from individual to individual, depending on the severity of the respiratory disease, the symptoms present, and other relevant variables; thus, single or multiple doses can be administered to an individual.

As disclosed herein, the invention contemplates the use of both concentrated and dilute surfactant compositions, depending upon the particular use, as described further herein. Concentrated surfactant compositions are typically used for "bolus" type administrations, whereas dilute surfactant compositions are typically used for "lavage" type administrations.

Typically, a concentrated surfactant has from 20 to 200 milligrams (mg) of active surfactant compound per milliliter (ml), more preferably about 25 to 100 mg/ml. A typical dilute surfactant has active surfactant compound at a concentration of from about 0.1 to 20 mg/ml, and more preferably about 0.5 to 10 mg/ml.

Polypeptides suitable for preparing surfactants in accordance with the present invention are further described in Section D below.

D. Proteins and Polypeptides

A protein or polypeptide of the present invention (subject protein or polypeptide) is characterized by its amino acid residue sequence and novel functional properties. A subject protein or polypeptide when admixed with a pharmaceutically acceptable phospholipid forms a pulmonary surfactant having a surfactant activity greater than the surfactant activity of the phospholipid or phospholipid and lipid alone. For example, a protein or polypeptide having a surfactant activity exhibits a lower ΔP when measured in a surfactant.

It is also to be understood that molecules comprising 60 or more amino acid residues, i.e., protein molecules, can be useful in surfactant compositions according to the present invention. While the present disclosure focuses primarily upon polypeptide molecules and molecules including amino acid residues, analogs, and/or other organic molecules, proteins having alternating hydrophobic and hydrophilic amino acid residue regions and proteins having surfactant ability as described herein are also contemplated by, and encompassed by, the present disclosures.

Molecules demonstrating surfactant activity which comprise 10 or fewer amino acid residues are also contemplated by the present invention. For example, a molecule comprising five amino acid residues linked to five amino acid derivatives or analogs can be useful as disclosed herein, particularly if it has alternating hydrophobic and hydrophilic amino acid residue regions and has surfactant ability, as defined herein. Thus, molecules comprising two to 100 amino acid residues having a configuration that maximizes their interaction with the alveoli are contemplated by the present invention. While larger molecules are somewhat more difficult to synthesize, it should be appreciated by those of skill in the relevant art that, as disclosed herein, even molecules containing 60 or more amino acid residues (or their analogs) can be excellent surfactants, provided they possess the disclosed characteristics.

Polypeptides suitable for preparing lipid-based surfactants in accordance with the present invention can be synthesized from amino acids by techniques that are known to those skilled in the polypeptide art. Summary of the many techniques available can be found, for example, in Steward and Young, 1969, *Solid Phase Peptide Synthesis, W.H. Freeman Co., San Francisco*, 1969, and Meienhofer, 1983, *Hormonal Proteins and Peptides*, Vol. 2, p. 46, Academic Press, New York, for solid phase peptide synthesis, and Schroder and Kubke, 1965, *The Peptides*, Vol. 1, Academic Press, New York, for classical solution synthesis.

In general, these methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group (e.g., lysine).

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and any solid support) are removed sequentially or concurrently, to afford the final polypeptide. That polypeptide is then washed by dissolving in a lower aliphatic alcohol, and dried. The dried surfactant polypeptide can be further purified by known techniques, if desired. (Various methods of preparing polypeptides of the present invention are also described in WO 89/06657; WO 92/22315; WO 98/49191; U.S. Pat. Nos. 5,260,273; 5,164,369; 5,407,914; 5,789,381; 5,952,303; 6,013,619; 6,013,764; 6,120,795; and 6,613,734; all of which are expressly incorporated by reference in their entirety for all purposes). In some embodiments, the surfactant polypeptides are polypeptides that include amino acid residue sequences having alternating charged and uncharged amino acid residue regions. Polypeptides including amino acid residue sequences having alternating hydrophobic and hydrophilic amino acid residue regions are also preferred according to the present invention. Particularly preferred surfactant polypeptides within these groupings are further characterized as having at least about 4, more preferably at least about 8, and even more preferably at least about 10, amino acid residues, and are generally not more than about 60 amino acid residues in length.

In other embodiments, surfactant polypeptides of the present invention are constituted by alternating groupings of charged amino acid residues and uncharged amino acid residues as represented by the formula $[(\text{Charged})_a(\text{Uncharged})_b]_c(\text{Charged})_d$, wherein a has an average value of about 1 to about 5; b has an average value of about 3 to about 20; c is 1 to 10; and d is 0 to 3. Organic surfactant molecules not comprised solely of amino acid residues alone preferably have a similar structure constituted by alternating groupings of charged and uncharged (or hydrophilic/hydrophobic) constituent molecules.

In one preferred embodiment, surfactant polypeptides include a sequence having alternating groupings of amino acid residues as represented by the formula $(Z_aJ_b)_cZ_d$, wherein Z is an amino acid residue independently selected from the group consisting of R, D, E, and K; J is an α-aminoaliphatic carboxylic acid; a has an average value of about 1 to about 5; b has an average value of about 3 to about 20; c is 1 to 10; and d is 0 to 3.

In another embodiment, preferred polypeptides of the present invention have alternating groupings of amino acids residue regions as represented by the formula $(B_aU_b)_cB_d$, wherein B is an amino acid residue independently selected from the group consisting of H, 5-hydroxylysine, 4-hydroxyproline, and 3-hydroxyproline; and U is an amino acid residue independently selected from the group consisting of V, I, L, C, Y, and F. In one preferred variation, B is an amino acid derived from collagen and is preferably selected from the group consisting of 5-hydroxylysine, 4-hydroxyproline, and 3-hydroxyproline; a has an average value of about 1 to about 5; b has an average value of about 3 to about 20; c is 1 to 10; and d is 0 to 3.

In still another preferred embodiment, surfactant polypeptides of the present invention include a sequence having alternating groupings of amino acid residues as represented by the formula $(B_aJ_b)_cB_d$, wherein B is an amino acid residue independently selected from the group consisting of H, 5-hydroxylysine, 4-hydroxyproline, and 3-hydroxyproline; and J is an α-aminoaliphatic carboxylic acid; a has an average value of about 1 to about 5; b has an average value of about 3 to about 20; c is 1 to 10; and d is 0 to 3.

In various embodiments including "J" in the relevant formula, J is an α-aminoaliphatic carboxylic acid having four to six carbons, inclusive. In other preferred variations, J is an α-aminoaliphatic carboxylic acid having six or more carbons, inclusive. In yet other variations, J is preferably selected from the group consisting of α-aminobutanoic acid, α-aminopentanoic acid, α-amino-2-methylpropanoic acid, and α-aminohexanoic acid.

Another preferred embodiment discloses surfactant polypeptides including a sequence having alternating groupings of amino acid residues as represented by the formula $(Z_aU_b)_cZ_d$, wherein Z is an amino acid residue independently selected from the group consisting of R, D, E, and K; and U is an amino acid residue independently selected from the group consisting of V, I, L, C, Y and F; from the group consisting of V, I, L, C and F; or from the group consisting of L and C; a has an average value of about 1 to about 5; b has an average value of about 3 to about 20; c is 1 to 10; and d is 0 to 3.

In the foregoing formulae, Z and U, Z and J, B and U, and B and J are amino acid residues that, at each occurrence, are independently selected. In addition, in each of the aforementioned formulae, a generally has an average value of about 1 to about 5; b generally has an average value of about 3 to about 20; c is 1 to 10; and d is 0 to 3.

In one variation of the foregoing embodiments, Z and B are charged amino acid residues. In other preferred embodiments, Z and B are hydrophilic or positively charged amino acid residues. In one variation, Z is preferably selected from the group consisting of R, D, E and K. In a related embodiment, Z is preferably selected from the group consisting of R and K. In yet another preferred embodiment, B is selected from the group consisting of H, 5-hydroxylysine, 4-hydroxyproline, and 3-hydroxyproline. In one preferred embodiment, B is H. In another preferred embodiment, B is a collagen constituent amino acid residue and is selected from the group consisting of 5-hydroxylysine, (6-hydroxylysine), 4-hydroxyproline, and 3-hydroxyproline.

In various disclosed embodiments, U and J are, preferably, uncharged amino acid residues. In another preferred embodiment, U and J are hydrophobic amino acid residues. In one embodiment, U is preferably selected from the group consisting of V, I, L, C, Y, and F. In another preferred embodiment, U is selected from the group consisting of V, I, L, C, and F. In yet another preferred embodiment, U is selected from the group consisting of L and C. In various preferred embodiments, U is L.

Similarly, in various embodiments, B is an amino acid preferably selected from the group consisting of H, 5-hydroxylysine, 4-hydroxyproline, and 3-hydroxyproline. Alternatively, B can be selected from the group consisting of collagen-derived amino acids, which includes 5-hydroxylysine, 4-hydroxyproline, and 3-hydroxyproline.

In another embodiment of the present invention, charged and uncharged amino acids are selected from groups of modified amino acids. For example, in one preferred embodiment, a charged amino acid is selected from the group consisting of citrulline, homoarginine, or ornithine, to name a few examples. Similarly, in various preferred embodiments, the uncharged amino acid is selected from the group consisting of α-aminobutanoic acid, α-aminopentanoic acid, α-amino-2-methylpropanoic acid, and α-aminohexanoic acid.

In preferred embodiments of the present invention, items "a", "b", "c" and "d" are numbers which indicate the number of charged or uncharged residues (or hydrophilic or hydrophobic residues). In various embodiments, "a" has an average value of about 1 to about 5, preferably about 1 to about 3, more preferably about 1 to about 2, and even more preferably, 1.

In various embodiments, "b" has an average value of about 3 to about 20, preferably about 3 to about 12, more preferably about 3 to about 10, even more preferably in the range of about 4-8. In one preferred embodiment, "b" is about 4.

In various embodiments, "c" is 1 to 10, preferably 2 to 10, more preferably in the range of 3-8 or 4-8, and even more preferably 3 to 6. In one preferred embodiment, "c" is about 4.

In various embodiments, "d" is 0 to 3 or 1 to 3. In one preferred embodiment, "d" is 0 to 2 or 1 to 2; in another preferred embodiment, "d" is 1.

By stating that an amino acid residue, e.g., a residue represented by Z or U, is independently selected, it is meant that at each occurrence, a residue from the specified group is selected. That is, when "a" is 2, for example, each of the hydrophilic residues represented by Z will be independently selected and thus can include RR, RD, RE, RK, DR, DD, DE, DK, and the like. By stating that "a" and "b" have average values, it is meant that although the number of residues within the repeating sequence (e.g., $Z_aU_b$) can vary somewhat within the peptide sequence, the average values of "a" and "b" would be about 1 to about 5 and about 3 to about 20, respectively.

For example, using the formula $(Z_aU_b)_cZ_d$ for the peptide designated "KL8" in Table 2 below, the formula can be rewritten as $K_1L_8K_1L_8K_1L_2$, wherein the average value of "b" is six [i.e., (8+8+2)/3=6], c is three and d is zero.

Exemplary preferred polypeptides of the above formula are shown in Table 2 below:

TABLE 2

| Designation[1] | SEQ ID NO: | Amino Acid Sequence |
|---|---|---|
| KL4 | 1 | KLLLLKLLLLKLLLLKLLLLK |
| KL8 | 2 | KLLLLLLLLKLLLLLLLLKLL |
| KL7 | 3 | KKLLLLLLLLKKLLLLLLLKKL |
| DL4 | 4 | DLLLLDLLLLDLLLLDLLLLD |
| RL4 | 5 | RLLLLRLLLLRLLLLRLLLLR |
| RL8 | 6 | RLLLLLLLLRLLLLLLLLRLL |
| RL7 | 7 | RRLLLLLLLLRRLLLLLLLRRL |
| RCL1 | 8 | RLLLLCLLLRLLLLCLLLR |
| RCL2 | 9 | RLLLLCLLLRLLLLCLLLRLL |
| RCL3 | 10 | RLLLLCLLLRLLLLCLLLRLLLLCLLLR |
| HL4 | 11 | HLLLLHLLLLHLLLLHLLLLH |

[1]The designation is an abbreviation for the indicated amino acid residue sequence.

Also suitable are composite polypeptides of about 4 to 60 amino acid residues having a configuration that maximizes their interaction with the alveoli. A composite polypeptide consists essentially of an amino terminal sequence and a carboxy terminal sequence. The amino terminal sequence has an amino acid sequence of a hydrophobic region polypeptide or a hydrophobic peptide of this invention, preferably hydrophobic polypeptide, as defined in the above formula. The carboxy terminal sequence has the amino acid residue sequence of a subject carboxy terminal peptide.

Proteins and polypeptides derived from or having characteristics similar to those of natural Surfactant Protein (SP) are useful in the present methods. As noted, SP isolated from any mammalian species can be utilized, although bovine, porcine and human surfactants are particularly preferred.

Natural surfactant proteins include SP-A, SP-B, SP-C or SP-D, or fragments thereof, alone or in combination with lipids. A preferred fragment is the amino-terminal residues 1-25 of SP-B.

A related peptide is the WMAP-10 peptide (Marion Merrell Dow Research Institute) having the sequence succinyl-Leu-Leu-Glu-Lys-Leu-Leu-Gln-Trp-Lys-amide (SEQ ID NO:15). Alternative peptides are polymers of lysine, arginine or histidine that induce a lowering of surface tension in admixtures of phospholipids as described herein.

In addition, human SP18 (SP-B) surfactant protein can be utilized as described herein. See, e.g., WO 89/06657; WO 92/22315; WO 98/49191; U.S. Pat. Nos. 5,260,273; 5,164,369; 5,407,914; 5,789,381; 5,952,303; 6,013,619; 6,013,764; 6,120,795; and 6,613,734; all of which are expressly incorporated by reference in their entirety for all purposes)

Thus, in one preferred embodiment, a surfactant molecule of the present invention comprises a polypeptide. In one variation, a surfactant polypeptide comprises about 4, more preferably about 10, amino acid residues. In various embodiments, a surfactant polypeptide preferably comprises 60 or fewer amino acid residues, more usually fewer than about 35, and even more preferably, fewer than about 25 amino acid residues. In various preferred embodiments, subject polypeptides correspond to the sequence of SP18 monomer, e.g., a single group of contiguous residues in the linear sequence of SP18. In other embodiments, subject polypeptides preferably have alternating charged and uncharged amino acid residue regions or have alternating hydrophobic and hydrophilic amino acid residue regions.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). The term "conservative substitution" also includes the use of a substituted amino acid in place of an unsubstituted parent amino acid provided that such a polypeptide also displays the requisite binding activity.

Additional residues can be added at either terminus of a polypeptide of the present invention, such as for the purpose of providing a "linker" by which such a polypeptide can be conveniently affixed to a label or solid matrix, or carrier. Labels, solid matrices and carriers that can be used with the polypeptides of this invention are known in the art; some examples are also described herein.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-$NH_2$ acylation, e.g., acetylation, or thioglycolic acid amidation, terminal-carboxlyamidation, e.g., ammonia, methylamine, and the like.

In another embodiment, a polypeptide of this invention has amino acid residue sequence that has a composite hydrophobicity of less than zero, preferably less than or equal to −1, more preferably less than or equal to −2. These hydrophobic polypeptides perform the function of the hydrophobic region of SP8. Thus, in one preferred embodiment, the amino acid sequence mimics the pattern of charged and uncharged—or hydrophobic and hydrophilic—residues of SP18.

It should be understood, however, that polypeptides and other surfactant molecules of the present invention are not limited to molecules having sequences like that of native SP18. On the contrary, some of the most preferred surfactant molecules of the present invention have little resemblance to SP18 with respect to a specific amino acid residue sequence, except that they have similar surfactant activity and alternating charged/uncharged (or hydrophobic/hydrophilic) residue sequences.

One disclosed embodiment of the present invention comprises a peptide-containing preparation, the 21-residue peptide being a mimic of human SP-B consisting of repeated units of four hydrophobic leucine (L) residues, bounded by basic polar lysine (K) residues. This exemplary peptide, which is abbreviated herein as "$KL_4$," (or "KL4") has the following amino acid residue sequence:

KLLLLKLLLLKLLLLKLLLLK.        (SEQ ID NO 1)

Combined with the phospholipids dipalmitoyl phosphatidylcholine and palmitoyl-, oleoylphosphatidyl glycerol (3:1) and palmitic acid, the phospholipid-peptide aqueous dispersion has been named "$KL_4$-Surfactant," and it is generally referred to herein in that manner. The efficacy of $KL_4$-Surfactant in various experimental and clinical studies has been previously reported. See, e.g., Cochrane and Revak, 1991, *Science* 254: 566-568; Vincent et al., 1991, *Biochemistry* 30:8395-8401; Cochrane et al., 1996, *Am J Resp & Crit Care Med,* 152:404-410; and Revak et al., 1996, *Ped. Res.* 39:715-724.

E. Amino Acids, Natural Metabolites, Derivatives, Designed Analogs, and Other Organic Molecules Surfactant molecules of the present invention also include organic molecules having surfactant activity, as defined above and as further described herein. While polypeptides and proteins are often described as exemplary, it should be understood that surfactant molecules of the present invention are not limited to those having either conventional amino acid side chains or a polyamide backbone structure.

As noted previously, the present invention contemplates a variety of surfactant molecules, including proteins, polypeptides, and molecules including amino acid residues, as well as a variety of surfactant compositions. While one tends to think of the "common" natural amino acids (i.e., those listed in Table 1; see Section A above) as being preferred for use in biological compositions, it is also true that a wide variety of other molecules, including uncommon but naturally occurring amino acids, metabolites and catabolites of natural amino acids, substituted amino acids, and amino acid analogs, as well as amino acids in the "D" configuration, are useful in molecules and compositions of the present invention. In addition, "designed" amino acid derivatives, analogs and mimics are also useful in various compounds, compositions and methods of the present invention, as well as polymers including backbone structures composed of non-amide linkages.

For example, in addition to the L-amino acids listed in Section A above, amino acid metabolites such as homoarginine, citrulline, ornithine, and α-aminobutanoic acid are also useful in molecules and compositions of the present invention. Thus, in the various formulas described above, "Charged", Z, or B can comprise homoarginine, citrulline, or ornithine, as well as a variety of other molecules as identified herein. Similarly, J can comprise α-aminobutanoic acid (also known as α-aminobutyric acid), α-aminopentanoic acid, α-aminohexanoic acid, and a variety of other molecules identified herein.

Further, substituted amino acids which are not generally derived from proteins, but which are known in nature, are useful as disclosed herein, include the following examples: L-canavanine; 1-methyl-L-histidine; 3-methyl-L-histidine; 2-methyl L-histidine; α,ε-diaminopimelic acid (L form, meso form, or both); sarcosine; L-ornithine betaine; betaine of histidine (herzynine); L-citrulline; L-phosphoarginine; D-octopine; o-carbamyl-D-serine; γ-aminobutanoic acid; and β-lysine. D-amino acids and D-amino acid analogs, including the following, are also useful in proteins, peptides and compositions of the present invention: D-alanine, D-serine, D-valine, D-leucine, D-isoleucine, D-alloisoleucine, D-phenylalanine, D-glutamic acid, D-proline, and D-allohydroxyproline, and the like. The foregoing can also be used in surfactant molecules according to the present invention; particularly preferred for use accordingly are those corresponding to the formula $\{(Charged)_a(Uncharged)_b\}_c(Charged)_d$.

The present invention also discloses that an extensive variety of amino acids, including metabolites and catabolites thereof, can be incorporated into molecules which display a surfactant activity. For example, molecules such as ornithine, homoarginine, citrulline, and a-aminobutanoic acid are useful components of molecules displaying surfactant activity as described herein. Surfactant molecules according to the present invention can also comprise longer straight-chain molecules; α-aminopentanoic acid and α-aminohexanoic acid are two additional examples of such useful molecules.

It should also be appreciated that the present invention encompasses a wide variety of modified amino acids, including analogs, metabolites, catabolites, and derivatives, irrespective of the time or location at which modification occurs. In essence, one can place modified amino acids into three categories: (1) catabolites and metabolites of amino acids; (2) modified amino acids generated via posttranslational modification (e.g., modification of side chains); and (3) modifications made to amino acids via non-metabolic or non-catabolic processes (e.g., the synthesis of modified amino acids or derivatives in the laboratory).

The present invention also contemplates that one can readily design side chains of the amino acids of residue units that include longer or shortened side chains by adding or subtracting methylene groups in either linear, branched chain, or hydrocarbon or heterocyclic ring arrangements. The linear and branched chain structures can also contain non-carbon atoms such as S, O, or N. Fatty acids can also be useful constituents of surfactant molecules herein. The designed side chains can terminate with (R') or without (R) charged or polar group appendages.

In addition, analogs, including molecules resulting from the use of different linkers, are also useful as disclosed herein. Molecules with side chains linked together via linkages other than the amide linkage, e.g., molecules containing amino acid side chains or other side chains (R— or R'—) wherein the components are linked via carboxy- or phospho-esters, ethylene, methylene, ketone or ether linkages, to name a few examples, are also useful as disclosed herein. In essence, any amino acid side chain, R or R' group-containing molecule can be useful as disclosed herein, as long as the molecule includes alternating hydrophilic and hydrophobic residues (i.e., component molecules) and displays surfactant activity as described herein.

The present invention also contemplates molecules comprising peptide dimers joined by an appropriate linker, e.g., peptide dimers linked by cysteine molecules. (As those of skill in the art are aware, two cysteine molecules can be linked together by a disulfide bridge formed by oxidation of their thiol groups). Such linkers or bridges can thus cross-link different polypeptide chains, dimers, trimers, and the like. Other useful linkers which can be used to connect peptide dimers and/or other peptide multimers include those listed above, e.g., carboxy- or phospho-ester, ethylene, methylene, ketone or ether linkages, and the like.

While it is appreciated that many useful polypeptides disclosed herein, e.g., the $KL_4$ polypeptide (SEQ ID NO:1), comprise naturally-occurring amino acids in the "L" form which are joined via peptide linkages, it should also be understood that molecules including amino acid side chain analogs, non-amide linkages (e.g., differing backbones) can also display a significant surfactant activity and can possess other advantages, as well. For example, if it is desirable to construct a molecule (e.g., for use in a surfactant composition) that is not readily degraded, one can wish to synthesize a polypeptide molecule comprising a series of D-amino acids.

"Polypeptoids" are a class of non-natural, sequence-specific polymers representing an alternative derivative of a peptide backbone. Structurally, they differ from polypeptides in that their sidechains are pendant groups of the amide nitrogen rather than the α-carbon (see, e.g., Simon et al., 1992, *Proc. Natl. Acad. Sci. U.S.A.* 89:9367-9371 and Zuckermann et al., 1992, *J. Am. Chem. Soc.* 114:10646-10647). "Retropeptoids" are believed to have a higher probability of bioactivity when protein binding is required, as the relative positioning of sidechains and carbonyls "line up" more closely with peptides (Kruijtzer, J. A, 1995 *Tetrahedron Letters* 36:6969-72). N-Substitution prevents proteolysis of the peptoid backbone (see, e.g., Miller et al., 1995, *Drug Dev Res* 35:20-32), giving enhanced biostability. Since polypeptoids are not proteolyzed, they are not strongly immunogenic (Borman, 1998, *C & E News* 76:56-57).

In another variation, one can wish to construct a molecule that adopts a more "rigid" conformation; one means of accomplishing this would be to add methyl or other groups to the a carbon atom of the amino acids.

As noted above, other groups besides a $CH_3$ group can be added to the a carbon atom, that is, surfactant molecules of the present invention are not limited to those incorporating a $CH_3$ at the α carbon alone. For example, any of the side chains and molecules described above can be substituted for the indicated $CH_3$ group at the α carbon component.

As used herein, "analogs" and "derivatives" of polypeptides and amino acid residues are intended to encompass metabolites and catabolites of amino acids, as well as molecules which include linkages, backbones, side-chains or side-groups which differ from those ordinarily found in what are termed "naturally-occurring" L-form amino acids. (The terms "analog" and "derivative" can also conveniently be used interchangeably herein). Thus, D-amino acids, molecules which mimic amino acids and amino acids with "designed" side chains (i.e., that can substitute for one or more amino acids in a molecule having surfactant activity) are also encompassed by the terms "analogs" and "derivatives" herein.

A wide assortment of useful surfactant molecules, including amino acids having one or more extended or substituted R or R' groups, is also contemplated by the present invention.

Again, one of skill in the art should appreciate that one can make a variety of modifications to individual amino acids, to the linkages, and/or to the chain itself, which modifications will produce molecules falling within the scope of the present invention, as long as the resulting molecule possesses surfactant activity as described herein.

F. Treatment Regimes

The invention provides pharmaceutical compositions comprising a pulmonary surfactant for the treatment of a respiratory disease, e.g., ARDS and RDS, formulated together with a pharmaceutically acceptable carrier. Some compositions include a combination of multiple (e.g., two or more) surfactants of the invention.

In prophylactic applications, pharmaceutical compositions or medicaments are administered to a patient susceptible to, or otherwise at risk of a disease or condition (i.e., a respiratory disease or disorder) in an amount sufficient to eliminate or reduce the risk, lessen the severity, or delay the outset of the disease, including biochemical, histological and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical and/or histological), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved. Typically, the response is monitored and repeated dosages are given if the response starts to wane.

G. Effective Dosages

Effective doses of a pulmonary surfactant for the treatment of disease, e.g., respiratory disease or disorder such as ARDS and RDS, as described herein, vary depending upon many different factors, including means of administration, target site, physiological state of the patient, whether the patient is human or an animal, other medications administered, and whether treatment is prophylactic or therapeutic. Usually, the patient is a human but nonhuman mammals can also be treated.

Dosing is dependent on severity and responsiveness of the disease state to be treated, with the course of treatment lasting from days to several days to several months, or until a cure is effected or a diminution of the disease state is achieved. Optimal dosing schedules can be calculated from measurements of drug accumulation in the body of a patient or subject. Persons of ordinary skill can easily determine optimum dosages, dosing methodologies and repetition rates. Optimum dosages can vary depending on the relative potency of individual surfactants and, in the case of concomitant administration, the relative potency of known drugs or other surfactants used in the treatment of disease. Optimum dosages can generally be estimated based on $EC_{50}$s found to be effective in in vitro and in vivo animal models.

In general, dosage is from 0.01 µg to 100 g per kg of body weight and can be given once or more daily, weekly, monthly or yearly, or even once every 2 to 20 years. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime. An optimal dosing schedule is used to deliver a therapeutically effective amount of the nucleic acid being administered via a particular mode of administration.

The term "therapeutically effective amount" as used herein refers to a characteristic of an amount of a therapeutic compound, or a characteristic of amounts of combined therapeutic compounds in combination therapy. The amount or combined amounts achieve the goal of preventing, avoiding, reducing or eliminating the respiratory disease or condition. Although individual needs can vary, determination of optimal ranges for effective amounts of formulations is within the skill of the art. Human doses can be extrapolated from animal studies (*Remington's Pharmaceutical Sciences*, 20th ed., Gennaro, ed., Mack Publishing Co., Easton, Pa., 2000). Generally the dosage required to provide an effective amount of a formulation, which can be adjusted by one skilled in the art, will vary depending on the age, health, physical condition, weight, type and extend of the disease or disorder of the recipient, frequency of treatment, the nature of concurrent therapy (if any) and the nature and scope of the desired effect(s). For additional guidance regarding formulation, dose and administration regimen, see Berkow et al., 1997, *The Merck Manual Of Medical Information*, Home, ed., Merck Research Laboratories, Whitehouse Station, N.J.; Goodman et al., 1996, *Goodman & Gilman's the Pharmacological Basis of Therapeutics*, 9th ed. McGraw-Hill Health Professions Division, New York; Ebadi, 1998, *CRC Desk Reference of Clinical Pharmacology*, CRC Press, Boca Raton, Fla.; Katzung, 2001, *Basic & Clinical Pharmacology*, 8th ed. Lange Medical Books/McGraw-Hill Medical Pub. Division, New York; Speight et al., 1997, *AverV's Drug Treatment: A Guide to the Properties, Choice, Therapeutic Use and Economic Value of Drugs in Disease Management*, 4th ed. Adis International, Auckland/Philadelphia, Pa.

For diagnostic applications, a detectable amount of a composition of the invention is administered to a subject. A "detectable amount," as used herein to refer to a diagnostic composition, refers to a dose of such a composition that the presence of the composition can be determined in vivo following pulmonary administration.

Subjects that can be treated by the methods of the present invention include those suffering from a respiratory disease or disorder, and those at risk for developing a respiratory disease or disorder. At-risk individuals include, but are not limited to, individuals with a family history of respiratory disease or disorder, individuals who have previously been treated for respiratory diseases, and individuals presenting any other clinical indicia suggesting that they have an increased likelihood of developing the respiratory disease or disorder. Alternatively stated, an at-risk individual is any individual who is believed to be at a higher risk than the general population for developing a respiratory disease or disorder. The term "prophylactically effective amount" is meant to refer to an amount of a formulation which produces an effect observed as the prevention of the onset or recurrence of a respiratory disease or disorder. Prophylactically effective amounts of a formulation are typically determined by the effect they have compared to the effect observe when a second formulation lacking the active agent is administered to a similarly situated individual.

The compositions of the present invention can be administered either before or during pulmonary crises. Further, they can also be administered prior to single-lung, double-lung, or heart-lung transplant. In addition, it can be desirable to give the active compound to the subject over a long period as an adjunct to, e.g., the standard therapies for respiratory diseases and disorders.

Following successful treatment, it may be desirable to have the patient undergo maintenance therapy to prevent the recurrence of the disease state, wherein the surfactant or surfactants are administered in maintenance doses, ranging from 0.1 μg to 20 g per kg of body weight, once or more daily, weekly, monthly or yearly, or even once every 2 to 20 years. For example, in the case of an individual known or suspected of being prone to a respiratory disease or condition, prophylactic effects may be achieved by administration of preventative doses, ranging from 0.1 μg to 20 g per kg of body weight, once or more daily, weekly, monthly or yearly, or even once every 2 to 20 years.

The compositions of the present invention can include sterile aqueous solutions which can also include sterile aqueous solutions which can also contain buffers, diluents and other suitable additives. The pharmaceutical formulations, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both. The formulations can be presented in unit-dose or multi-dose containers, for example sealed ampoules and vials, and can be stored in a frozen or freeze-dried (lyophilized) condition requiring only the addition of sterile liquid carrier immediately prior to use.

When used as a pharmaceutical treatment, the compositions of the present invention can be administered either alone or optionally in conjunction with other compounds or compositions that are used in the treatment of respiratory diseases or disorders. For example, if a subject is being treated for a respiratory disorder caused by a bacterial infection, then a composition of the present invention may be administered in conjunction with another compound or treatment used to treat the bacterial infection, such as an antibiotic. Examples of such compounds, referred to herein as "supplemental compounds," or "supplemental compositions," include, but are not limited to, antibiotics, anti-cytokines, anti-asthma drugs, antiphospholipases (e.g., inhibitors of phospholipase), vasodilators (e.g., adenosine, .beta.-adrenergic agonists or antagonists, β-adrenergic blockers, α-adrenergic blockers, diuretics, smooth muscle vasodilators, nitrates, and angiotensin-converting enzyme inhibitors), and compounds found to be useful in the treatment of cystic fibrosis, such as pyrazinoylguanidine sodium channel blockers (e.g., amiloride, benzamil, phenamil).

The pharmaceutical compositions are generally formulated as sterile, substantially isotonic and in full compliance with all Good Manufacturing Practice (GMP) regulations of the U.S. Food and Drug Administration.

H. Therapeutic Methods

The present application also discloses a variety of therapeutic methods that are useful in conjunction with various novel compounds and compositions disclosed herein. While the use of $KL_4$-surfactant is described herein as exemplary, it should be understood that the other compounds and compositions disclosed herein, as well as compounds and compositions having surfactant activity and known to those of skill in the art, are also useful according to the described methods.

The surfactant compositions of the present invention, and therapeutic methods for pulmonary administration of the compositions to a subject, are useful for the treatment of a disease or disorder of the lung, such as an infection, an immunodeficiency syndrome, an inflammatory disease, an autoimmune disease, a neoplasm, or cancer. In particular, the present invention provides improved methods for formulating therapeutic proteins for pulmonary delivery.

The present invention also discloses preferred methods of treating respiratory diseases in patients of any age, including neonates and adults. One such method comprises administering to a patient in need of such treatment a therapeutically effective amount of a surfactant composition, preferably, a lipid-based surfactant composition, prepared from a polypeptide (or other surfactant molecule) of the present invention and a pharmaceutically acceptable phospholipid, wherein the polypeptide is combined with the phospholipid in an amount sufficient to increase the surfactant activity of the composition above that of the phospholipid. The present invention also discloses a method of treating respiratory diseases, for example ARDS and RDS, wherein the polypeptide is constituted by about 10-60 amino acid residues and alternating groupings of charged amino acid residues and uncharged amino acid residues as represented by the formula $[(\text{Charged})_a(\text{Uncharged})_b]_c(\text{Charged})_d$, wherein a has an average value of about 1 to about 5; b has an average value of about 3 to about 20; c is 1 to 10; and d is 0 to 3. In various preferred embodiments, such a polypeptide, when admixed with a pharmaceutically acceptable phospholipid, forms a pulmonary surfactant having a surfactant activity greater than the surfactant activity of the phospholipid alone.

As disclosed herein and as further described in the Examples set forth below, a variety of methods for administering the surfactant compounds and compositions of the present invention are available and are well known by one of skill in the art. Depending on the needs of any individual needing treatment, e.g., an infant or adult with respiratory distress syndrome, different treatment methods can be appropriate.

Thus, in instances in which an infant suffers from a respiratory disease, such as aspirated meconium, particular treatment modalities can be recommended. In one such therapeutic method, lavage of the patient's lungs with a surfactant composition of the present invention is performed. A single lavage with surfactant can be all that is required; alternatively, multiple surfactant lavages can be appropriate. Moreover, a saline lavage followed by one or more surfactant lavages can be an appropriate treatment, albeit that it will be shown below that dilute surfactant lavage tends to produce better results than a combination of saline and surfactant lavage.

Lavage procedures using surfactant are performed essentially as follows. $KL_4$-surfactant or another surfactant (e.g., one of the present invention) is preferably administered using tools typically used in saline lavage procedures, which include various flexible tube-like apparatus such as endotracheal tubes, cannulae and catheters. Thus, for example, an endotracheal tube apparatus which includes a cannula that can be inserted through the tube, e.g., for suctioning purposes, is appropriate for use according to the disclosed methods. Preferably, any apparatus appropriately used to safely and efficaciously deliver and remove lavage fluids to and from the lung, respectively, is contemplated for use herein.

Exemplary devices for pulmonary lavage are ventilator devices equipped for bronchoalveolar lavage (BAL), which must include a means for applying a positive end-expiratory pressure (PEEP) to the lung, a means for instilling liquids into the lung and a means for removing pulmonary fluids from the lung using negative pressure suction.

Representative devices are described in U.S. Pat. Nos. 4,895,719, 5,207,220, 5,299,566 and 5,309,903, the disclosures of which are hereby incorporated by reference in their entirety for all purposes.

As shown herein, particularly advantageous results were obtained by practicing a method of pulmonary lavage using dilute surfactant that produced sustained recovery of arterial oxygen ($PaO_2$), normal lung compliance and diminished inflammation following pulmonary injury by meconium aspiration or by partial loss of intrinsic surfactant, such as is demonstrated herein in the model using instillation of bacterial LPS. These methods can be useful for use in treating any of a variety of pulmonary conditions in which there is respiratory distress, particularly ARDS and RDS.

Conditions in which respiratory stress can be present include, but are not limited to, meconium aspiration in newborn infants, pulmonary inflammation, and pulmonary infection. Respiratory distress can be associated with a variety of conditions, including sepsis, pulmonary trauma, accumulation of pulmonary exudate, pancreatitis, aspiration of gastric contents, heated gas inhalation, smoke or noxious gas inhalation, acute hypoxemia, fetal circulation, congenital diaphramatic hernia, pneumonia, inflammation arising from infection or multiple transfusions, and the like.

As shown herein, the present dilute surfactant lavage methods remove mediators of inflammation and simultaneously preserve and/or restore pulmonary function, thereby providing effective therapy.

The application of the pulmonary lavage provides several beneficial features. The washing effect of the lavage removes debris, dead cells, loose inflammatory cells and fluids, and the like, cleaning the alveoli of occluding fluid and materials, and removing typically 30 to 95% of the pulmonary and lavage fluids, together with any undesirable materials, such as meconium or inflammatory exudates. The dilute surfactant treats the alveolar membranes, improving the compliance of the tissue. The application of specified amounts of ventilator air pressure in the form of positive end-expiratory pressure (PEEP) before, during and after lavage with surfactant expands the lungs to maximize contact in the wash and treatment phase and thereby improve the dynamics of the lavage process, and in particular improves the oxygen tension and gas exchange in the patient during a process that can precariously burden oxygen exchange in the alveoli. Finally, the use of short intervals of tracheo-bronchial suction to remove the pulmonary (lavage) fluids are carefully administered in a manner that does not allow the arterial oxygen saturation to be reduced below acceptable and safe levels.

The pulmonary lavage method can be practiced on any mammal, and is particularly suited for humans, including adults, juveniles and infants, both newborn infants and babies experiencing respiratory distress or suffering from a respiratory disease or disorder.

The method for pulmonary lavage of a mammal comprises applying vapor phase (gas) positive end-expiratory pressure (PEEP) with a ventilator means to a lung, lung section or lobe of the mammal. Thereafter, a lavage composition containing dilute surfactant in a pharmaceutically acceptable aqueous medium is instilled into the lung or lung section of the mammal. Afterwards, some or all pulmonary fluid, including the lavage composition, present in the lung section is removed by applying short intervals of tracheo-bronchial suction using negative pressure.

The PEEP is typically administered at a pressure range of 4 to 20 centimeters (cm) water, although the pressure can vary depending on the patient and the pulmonary condition. For adults, juveniles and infants other than newborns, in which the lungs have toughened, the range is preferably from 6 to 12 cm water, and more preferably about 8-10 cm water. For newborn infants in which the lung sacs are more delicate and more fragile to applied pressure, the PEEP can range from about 4 to 15 cm water, preferably about 6 to 9 cm water, and more preferably about 8 cm water.

The administration of gas PEEP is typically applied to the lung prior to instilling dilute surfactant lavage, typically for up to about 30 minutes prior, more preferably about 5 to 30 minutes, in order to stabilize the blood oxygen prior to the procedure. In addition, PEEP is preferably applied continuously throughout the procedure during both the instilling and removing steps. It is to be understood that the combined effect on pressure of applying continuous PEEP and a short interval of suction will result in a brief, transient, drop in net pressure, with a rapid return to the maintained PEEP level when the suction interval is terminated. In addition, PEEP can be applied for a time period after the lavage fluid removal step in order to maintain oxygen tension on the alveoli following the procedure. Preferably, PEEP is maintained for up to about 24 hours after the removing step, preferably up to about 12 hours, and more preferably about 0.5 to 6 hours.

It is also contemplated that the applied gas can contain supplemental oxygen, typically from about 21 to 100% oxygen, preferably about 50 to 100% oxygen.

The suction phase of the method to remove the lavage and pulmonary fluids is administered in short intervals, i.e, 1 to 120 seconds. A typical suctioning interval is less than 30 seconds, preferably less than 20 seconds, and more preferably for about 5 to 20 seconds. A preferred interval is from 2 to 120 seconds, and preferably 5 to 20 seconds. The suction time period is short in order to minimize decreases in and saturated arterial oxygen ($SaO_2$) that can accompany the suction phase of the lavage procedure.

In one permutation of the suction procedure where there is more than one suction step required to remove the pulmonary fluid, it is desirable to pause between short suction intervals rather than to follow one suction interval immediately with another in order to provide the opportunity for the $PaO_2$ level to recover. A typical pause period is from about 30 seconds to fifteen minutes, preferably about 1-5 minutes.

The suction applied to remove pulmonary fluids is a negative pressure of from about 10 to 150 millimeters (mm) mercury (Hg), preferably about 20 to 120 mm Hg, and more preferably about 60 to 100 mm Hg. A suction catheter or similar suction means is present in the ventilator device, typically as a cannula extending through the ventilator tube of the apparatus and into the bronchus. The cannula tip is typically guided into a segmental bronchus with the aid of the fiber optic observing means, and the instilling and removing are provided through the cannula tip.

In practicing the dilute lavage method, it is understood that the lavage can be administered repeatedly. Thus, the instilling and removing steps are repeated sequentially while applying PEEP as described herein. Typically, instilling and removing (lavage wash cycles) can be repeated in sequence from 2 to 5 times, although additional repetitions can be conducted if warranted. In addition, the content of the dilute surfactant can be varied over the course of the repeated lavage washes. For example, it is contemplated that a first series of from 1 to 3 wash cycles are conducted using dilute surfactant at a concentration of about 0.1 to 10 mg per ml lavage composition, and a second series of from 1 to 5 wash cycles are conducted using dilute surfactant at a concentration of about 10 to 50 mg per ml.

Depending on the position of the endotracheal tube apparatus in lung, the lavage composition will bathe a lung lobe, a lung segment or an entire side of lung, this being determined by the position in the bronchial tube where the apparatus terminates. Thus, it is understood that the term "lung" connotes alternatively that a lung lobe, a lung segment, a lung half containing two or three lobes, or a whole lung is being referred to in the context of the method, but adjusted for volume based on weight of the patient.

In instilling a lavage composition, it is also understood that the process can be conducted by a variety of methods, such as by cannula, by bronchoscope, by endotracheal tube and the like. In a preferred method, the instilling is typically monitored visually by a means for observing the lung at the apparatus tube terminus, typically by use of a fiber optic bronchoscope and illuminating means for visual display of the bronchial tube and distal lung lobe(s). Thus, although estimates of the appropriate lavage composition volume are stated, it is understood that in practice, the instilled volume can depend on the judgment of the practitioner during the instilling process, aided by the observing means.

The pulmonary lavage process is typically conducted on as many lungs, both left and right, and involved lung lobes, as needed depending on the extent of the condition of the lungs. Typically the procedure is conducted sequentially on 30 to 100% of the bronchial segments of the left and right lungs.

The bronchoscope or endotracheal tube can be fitted with a fixed or expanding collar designed to fit the inner diameter of a bronchial passage, and thereby secure a fit that can withstand the pressure ranges for practicing the method. This feature is particularly desirable insofar as it allows a section of the lung to be lavaged while the remaining lung portions can respire, thereby minimizing the trauma of the procedure to gas exchange in the patient.

$KL_4$-surfactant solution or other novel surfactant solutions according to the present invention can be administered via lavage in a formulation appropriate for this procedure. While a formulation of surfactant comprising about 10-20 ml/kg is useful in the treatment of respiratory diseases such as ARDS and RDS, formulations for lavage therapy tend to be more dilute, to facilitate efficient delivery and removal via endotracheal tube.

Thus, a "dilute surfactant" when used in the context of a lavage composition indicates that the lavage composition contains one or more substances which provide surfactant activity to the composition as defined herein in an amount sufficient to provide the surfactant activity but present in an amount such that the composition has a liquid viscosity amenable to lavage.

Thus, a surfactant-containing composition useful for administration to a subject (or patient) via lavage is preferably diluted to a concentration of about up to about 100 mg/ml so long as the viscosity is such that the composition is amenable to suction removal in less than 30 seconds following instillation. Dosages in the range of about 0.1-100 mg/ml are typically contemplated for use herein. In addition, the administration of higher dosages can be appropriate in various instances, e.g., when the subject is not fully responsive to lower dosages, or where the formulation lowers viscosity while allowing for increased concentrations of surfactant activity-containing substances.

In general, quantities of surfactant of about 4 to 60 ml per kg of the subject's (or patient's) body weight are given during each administration, typically divided equally between right lung and left lung or divided among lung sections. Depending on the needs of the individual patient, which can readily be determined by the physician or other individual of skill in the relevant art who is administering the treatment, greater or lesser quantities of surfactant can be delivered during each administration. Quantities comprising about 8-30 ml/kg are preferred, with quantities comprising about 10-25 ml/kg being somewhat more preferred. Thus, lavage composition is typically instilled in a volume of about 4 to 60 ml per kilogram (kg), preferably about 8 to 30 ml per kg, and more preferably about 16-25 ml per kg.

In describing the amount of surfactant present in a lavage composition, the weight refers to an amount measured as phospholipid phosphate per total volume of lavage composition, unless otherwise specified.

The amount of surfactant administered via lavage can also be described "per lung" in a particular patient. Thus, an effective amount of surfactant for lavage purposes can comprise about 200-1000 ml/lung for a 70 kg adult, preferably about 400 ml/lung, and about 30-60 ml/lung for a 3 kg infant, preferably about 50 ml/lung. As before, depending on the maturity and size of the individual receiving treatment, the amount of surfactant administered, as well as the dosage, can be adjusted as appropriate.

A subject can receive one or more lavages, depending on the severity of the individual's condition and depending on the response of the subject to the first lavage. The dosages and amounts of surfactant administered can likewise vary in subsequent lavages. For example, if a subject receives a typical dose during the first lavage, subsequent lavages can be administered using the same dosage, a lesser dosage, or a higher dosage, depending on the needs and response of the subject.

Similarly, the amounts of surfactant administered during each lavage can vary, or can remain constant, depending on the needs of the individual patient. In appropriate circumstances, the first or subsequent lavage can be followed by a lavage administering a higher dose, e.g., up to 10-50 mg/ml. For example, a subject can receive 1-3 lavages with surfactant at a concentration of 0.1-10 mg/ml followed by 1-5 ravages with surfactant at a concentration of 10-50 mg/ml.

As noted previously, the dosage to be administered varies with the size and maturity of the subject, as well as with the severity of the subject's condition. Those of skill in the relevant art will be readily able to determine these factors and to adjust the dosage administered via lavage, as taught herein.

Bolus administration of surfactant can also be appropriate. Thus, for example, a bolus of 10-300 mg/kg surfactant at 15-100 mg/ml can be administered prior to or subsequent to one or more lavage treatments.

The type of treatment, dosage and amount utilized will understandably vary depending on the nature and seriousness of an individual subject's condition. Thus, for example, if a subject is an infant suffering from meconium aspiration, a treatment regimen comprising one or more surfactant lavages will likely be administered. Bolus administration of surfactant can follow the lavage(s) as well.

As noted previously, one aspect of the present invention was the removal of meconium or inflammatory exudate from the airways via lavage with dilute surfactant, in order to improve pulmonary function and inhibit the inflammatory reaction that usually develops in response to the presence of meconium or other injurious substances in the respiratory pathway. Although many of the examples focus on the use of one preferred embodiment, e.g., a synthetic peptide-containing exogenous surfactant, it is expressly to be understood that other surfactant-containing lavage compositions can be used according to the disclosed methods. Exemplary formulations for, and methods of using surfactants are also disclosed in the present specification.

The compositions of the present invention can be administered directly into the lungs of the subject by any suitable means, but preferably by intratracheal instillation, and more preferably bolus intratracheal instillation. An alternative preferred method of administration is via inhalation of respirable aerosol particles comprising the composition. Pulmonary lavage is another alternative route of administration as discussed above. Accordingly, the composition can be administered, as appropriate to the dosage form, by endotracheal tube, by bronchoscope, by cannula, by aerosol administration, or by nebulization of a suspension or dust of the composition into a gas to be inspired. Compositions of the present invention can also be delivered to the lung in an aerosolized form using the pulmonary drug delivery systems set forth in U.S. Pat. No. 5,874,064 and U.S. Pat. No. 5,934,273, the disclosures of which are herein incorporated by reference in their entireties for all purposes.

In one embodiment of the invention, the composition of the invention can be administered by administering an aerosol of respirable particles comprised of the composition, which the subject inhales. The composition can be aerosolized in a variety of forms, such as, but not limited to, dry powder inhalants, metered dose inhalants, bolus or continuously delivered liquid solutions or dispersions. The respirable particles can be liquid or solid. Solid or liquid particulate forms of the compositions prepared for practicing the present invention should include particles of respirable size: that is, particles of a size sufficiently small to pass through the mouth and larynx upon inhalation and into the bronchi and alveoli of the lungs. In general, particles ranging from about 0.5 to 5 microns in size are within the respirable range. In a preferred embodiment, the microparticles have a diameter between 0.5 microns and 5 microns mass median aerodynamic diameter and viscosity less than 10 cp (measured at room temperature) at a cholesterol concentration from about 8 mole % to about 15 mole %, in a pharmaceutically acceptable carrier for administration to the lungs. In another preferred embodiment, the microparticles have a diameter between 0.5 microns and 5 microns and viscosity less than 30 cP at a cholesterol concentration from about 8 mole % to about 15 mole %, in a pharmaceutically acceptable carrier for administration to the lungs. As described herein, the viscosity less than 30 cP can be defined as the fluid viscosity at 25° C. using an instrumented cone and plate viscometer operating at a rate of approximately 160 $sec^{-1}$. A step-flow procedure can be employed that involves increasing the spin rate from about 0 to 200 $sec^{-1}$ allowing the viscosity to reach equilibrium after each of 10 steps and then repeating the process while decreasing the spin-rate.

Particles of non-respirable size that are included in the aerosol tend to be deposited in the throat and swallowed, and the quantity of non-respirable particles in the aerosol is preferably minimized. The particulate pharmaceutical composition can optionally be combined with a carrier to aid in dispersion or transport. A suitable carrier such as a sugar (i.e., lactose, sucrose, trehalose, and mannitol) can be blended with the active compound or compounds in any suitable ratio (e.g., a 1 to 1 ratio by weight).

Aerosols of liquid particles comprising the compositions can be produced by any suitable means, such as with a pressure-driven aerosol nebulizer or an ultrasonic nebulizer. See, e.g., U.S. Pat. No. 4,501,729. Nebulizers are commercially available devices that transform solutions or dispersions of the active compound (i.e., $KL_4$ surfactant) into a therapeutic aerosol mist by means of acceleration of compressed gas, typically air or oxygen, through a narrow enturi orifice, by means of ultrasonic agitation, by means of electrohydrodynamic, by liquid vaporization and condensation or by agitation through vibrating membranes. Suitable formulations for use in nebulizers consist of the active ingredient in a liquid carrier, the active ingredient comprising up to 40% w/w of the formulation, but preferably less than 20% w/w. The carrier medium is typically water-based (and most preferably sterile, pyrogen-free water) or a dilute aqueous alcoholic solution, preferably made isotonic but can be hypertonic or hypotonic relative to body fluids by the addition of, for example, sodium chloride. Optional additives include preservatives if the formulation is not made sterile, for example, methyl hydroxybenzoate, antioxidants, flavoring agents, volatile oils, buffering agents, and surfactants.

Aerosols of solid particles comprising the composition can likewise be produced with any solid particulate medicament aerosol generator. Aerosol generators for administering solid particulate medicaments to a subject produce particles that are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders that can be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin, plastic or aluminum foil, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

A second type of illustrative aerosol generator comprises a metered dose inhaler (MDI). MDIs are pressurized aerosol dispensers, typically containing a suspension or solution formulation of the active ingredient in a liquefied propellant. During use, these devices discharge the formulation through a valve adapted to deliver a metered volume, typically from 10 to 200 µl, to produce a fine particle spray containing the active ingredient. Suitable propellants include certain chlorofluorocarbon or hydrofluorocarbon compounds, for example, dichlorodifluoromethane, trichlorofluoromethane, dichlorotetrafluoroethane and mixtures thereof. The formulation can additionally contain one or more co-solvents, for example, ethanol, surfactants, such as oleic acid or sorbitan trioleate, antioxidants and suitable flavoring agents.

Any propellant can be used in carrying out the present invention, including both chlorofluorocarbon-containing propellants and non-chlorofluorocarbon-containing propellants. Thus, fluorocarbon aerosol propellants that can be employed in carrying out the present invention including fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants and mixtures thereof. Particularly preferred are hydrofluoroalkanes such as 1,1,1,2-tetrafluoroethane and heptafluoropropane. A stabilizer such as a fluoropolymer can optionally be included in formulations of fluorocarbon propellants, such as described in U.S. Pat. No. 5,376,359.

The aerosol, whether formed from solid or liquid particles, can be produced by the aerosol generator at a rate of from about 0.1 to 1 mL per minute. Aerosols containing greater amounts of medicament can be administered more rapidly. Typically, each aerosol can be delivered to the patient for a period from about 30 seconds to about 20 minutes, with a delivery period of about five to ten minutes being preferred.

Reperfusion is also associated with harmful effects of neutrophil activation and tissue infiltration. The nature of the neutrophil-mediated injury is not fully characterized but is in part due to the production of superoxide anion ($O_2$) and/or related oxidative products. This sequence of events (activation of white blood cells, release of toxic mediators, and resultant pathophysiology in the host) is common to many inflammatory diseases.

The present invention also provides compositions and methods for treating conditions associated with oxidative injury. For example, aerosol compositions comprising the compositions of the present invention together with drugs or other active agents known to reduce cell and/or tissue damage due to oxidative injury, and to inhibit oxidant production by leukocytes are contemplated. Tissue at risk of oxidative injury can include blood-perfused tissue and inflamed tissue.

Inflammatory diseases and disorders that can be treated using the disclosed compositions and methods include but are not limited to acute lung injury, acute respiratory distress syndrome, arthritis, asthma, bronchitis, cystic fibrosis, reperfusion injury artery occlusion, stroke, ultraviolet light induced injury, and/or vasculitis. The inflammation can be symptomatic of a separate disease or condition, such as autoimmune disease and transplantation. Inflammatory diseases and disorders also include those conditions characterized by leukocyte dysfunction. The inflammation can be acute, chronic, or temporary inflammation. See e.g., Weissmann et al., 1982, *Ann NY Acad Sci* 389:11-24, Goldstein et al., 1982, *Ann NY Acad Sci* 389:368-79, Janoff, 1985, *Annu Rev Med* 36:207-16, Hart & Fritzler, 1989, *J Rheumatol* 16:1184-91, Doring, 1994, Am J Respir Crit Care Med 150: S114-7, Demling, 1995, *Annu Rev Med* 46:193-202, Hansen, 1995, *Circulation* 91:1872-85, Dakik & Nasrallah, 2001, *Heart Dis* 3:362-4, Kehl et al., 1996, *Intensive Care Med* 22:968-71, and Munkvad, 1993, *Dan Med Bull* 40:383-408.

Reduced tissue inflammation can be assayed by detecting proteins induced by inflammation, such as cytokines, monokines, receptors, and proteases. For example, histamine can be measured using a fluorescent assay described by Shore et al., 1959, *J Pharmacol Exp Ther* 127:182-186. Nitric oxide can be measured using a chemiluminescent assay described by Hybertson, 1994, *Anal Lett* 127:3081-3093.

Reduced inflammation can also be assessed by measuring a reduction in oxidant production, including oxidant production by neutrophils, macrophages, monocytes eosinophils, mast cells and/or basophils. Representative methods for assaying the production of oxidants by inflammatory cells are described in the examples. Neutrophil function can also be assayed using techniques known in the art, for example, as described by Bell et al., 1990, *Br Heart J* 63:82-7, Riesenberg et al., 1995, *Br Heart J* 73:14-9, Zivkovic et al., 1995, *J Pharmacol Exp Ther* 272:300-9.

An aerosol composition of the invention can also comprise a detectable label. Preferably, the detectable label can be detected in vivo, for example by using any one of techniques including but not limited to magnetic resonance imaging, scintigraphic imaging, ultrasound, or fluorescence. Thus, representative detectable labels include fluorophores, epitopes, radioactive labels, and contrast agents.

In one embodiment of the invention, the detectable label is a protein, e.g., a fluorescent protein. Alternatively, the detectable label is conjugated to a protein to be administered. For example, a composition of the invention can comprise a diagnostic protein which is conjugated or otherwise bound to a detectable label. Representative detectable labels, labeling methods, and imaging systems suitable for pulmonary imaging and diagnosis are described, for example, in Desai, 2002, *Clin Radiol* 57:8-17, McLoud, 2002, *Clin Chest Med* 23:123-36, and McWilliams et al., 2002, *Oncogene* 21:6949-59.

In addition to being useful in methods of treating lung disorders (i.e., where the composition is a pharmaceutical composition), the compositions and methods of the present invention can be useful in enhancing pulmonary or airway function in subjects generally. In this embodiment, the subject is not necessarily suffering from a respiratory disease or disorder, but rather can be a subject who is generally physically healthy, but desires improvement in pulmonary function (i.e., easier breathing). Subjects can desire the administration of the compositions of the present invention in this context, for example, because of incidental exposure to cigarette smoke (primary or second-hand), environmental toxins or air pollution or smog; because of a decrease in pulmonary function due to normal aging processes; because of the desire for improved cardiovascular fitness, and the like. In this sense, the compositions of the present invention are administered not as a prescribed pharmaceutical (i.e., a drug), but rather as a general health-improving tonic. By "enhance" is meant that pulmonary function (e.g., respiration) occurs at an improved level, as compared to pulmonary function occurring with the lack of administration of the compositions of the present invention.

Pulmonary administration of a surfactant composition of the present invention can be combined with other techniques for pulmonary delivery, for example carbon dioxide enhancement of inhalation therapy (see, e.g., U.S. Pat. No. 6,440,393) and bronchodilation (see e.g., U.S. Pat. No. 5,674,860 and U.S. Published Patent Application No. 20020151597). A treatment regimen can also comprise pulmonary delivery with other delivery routes (e.g., oral and intravascular delivery).

I. Toxicity

Preferably, a therapeutically effective dose of the surfactant compositions described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1)

J. Kits

A further subject of the invention is a commercial product consisting of a customary secondary packaging, a primary packaging comprising a pharmaceutical preparation and, if desired, a pack insert, the pharmaceutical preparation being suitable for the prophylaxis or treatment of chronic respiratory diseases or disorders in patients and reference being made on the secondary packaging or on the pack insert of the commercial product to the suitability of the pharmaceutical preparation for the prophylaxis or treatment of respiratory diseases in patients, and the pharmaceutical preparation being a pulmonary surfactant formulation or preparation. The secondary packaging, the primary packaging comprising the pharmaceutical preparation and the pack insert otherwise correspond to what the person skilled in the art would regard as standard for pharmaceutical preparations of this type. Suitable primary packaging is, for example, ampoules or bottles of suitable materials such as transparent polyethylene or glass or alternatively suitable means of administration such as are customarily employed for the administration of active compounds into the lungs. By way of example, mention can be made of means of administration for the atomization of an active compound solution or suspension or for the atomization of active compound powder. Preferably, the primary packaging is a glass bottle which can be sealed, for example, by a commercially available rubber stopper or a septum. A suitable secondary packaging which may be mentioned by way of example is a folding box.

The kits of the invention can also include an inhalation apparatus, surfactant dry aerosol particle formulation and a detection system. An inhalation apparatus, as used herein, is any device for administering a dry aerosol. This type of equipment is well known in the art and has been described in detail, such as that description found in *Remington's Pharmaceutical Sciences*, 20th ed., 2000. Inhalation devices are described, for example, in U.S. Pat. No. 6,116,237.

The following examples are intended to illustrate, but not limit, the present invention.

EXEMPLARY EMBODIMENTS

Example 1

Development of Novel Lung Surfactant Formulation Containing DPPG and Cholesterol Formulation of Lung Surfactant: Lab-scale formulations were prepared at 60 mg/ml (TPL) with the cholesterol content variations described below (Table 3). Each formulation was prepared in n=1-5 (see lot numbers and names in Table 3) and individually characterized. The appropriate amounts (Table 3) of DPPC, POPG/DPPG, PA/cholesterol and $KL_4$ by weight were sequentially added to a round bottom flask containing appropriate volumes of ethanol, which was heated to 45-50° C. Each of the components was added with 1-2 minutes application of bath sonication. Finally, after each of components was added, the flask was bath sonicated for 5 more minutes. The flask was attached to a rotary evaporator and the ethanol was evaporated at 55° C. The speed of the rotary evaporator was ~50 rpm and a vacuum of <10 mbar was applied. When there was about 15 mls of ethanol remaining in the flask, the speed of the rotary evaporator was increased to 60 rpm in order to form a frothy film. On formation of a persistent film, the flask was placed in a vacuum desiccator for a period of 20 hrs in order to remove all the residual ethanol. The following day the formulations were hydrated with 20 mM Tris-Acetate buffer at a pH of 7.5 pre heated to ~25° C. The resulting aqueous dispersion was bath-sonicated at 45-50° C. with intermittent swirling of the flask over 30 mins. This resulted in a fine white dense dispersion. 5M NaCl was added under constant ultrasonication and shaking of the flask drop wise at 45-50° C. in order to obtain a final concentration of 130 mM of NaCl in the buffer. The ultrasonication was continued for 5 mins after complete addition of NaCl. This yielded a very fine homogeneous dense white dispersion. Table 3 summarizes the samples used for testing.

TABLE 3

Composition of formulations

| Formulation Lot | Formulation compositoin | Cholesterol mol (%) |
|---|---|---|
| A0170-10-0 | DPPC/DPPG 3/1 | 0 |
| A0170-5-01 | | 1 |
| A0154-22-01 | | 2 |
| A0170-5-02 | | 2 |
| A0170-14-2-1 | | 2 |
| A0170-14-2-2 | | 2 |
| A0170-14-2-3 | | 2 |
| A0154-22-02 | | 5 |
| A0170-5-05 | | 5 |
| A0154-22-03 | | 8 |
| A0170-5-08 | | 8 |
| A0170-15-8-1 | | 8 |
| A0170-15-8-2 | | 8 |
| A0170-15-8-3 | | 8 |
| A0154-22-04 | | 10 |
| A0170-5-10 | | 10 |
| A0170-14-10-1 | | 10 |
| A0170-14-10-2 | | 10 |
| A0170-14-10-3 | | 10 |
| A0170-5-12 | | 12 |
| A0170-5-15 | | 15 |
| A0170-10-20 | | 20 |
| A0170-10-25 | | 25 |
| A0170-15-30-1 | | 30 |
| A0170-15-30-2 | | 30 |
| A0170-12-0 | DPPC/POPG 3/1 | 0 |
| A0170-12-2 | | 2 |
| A0170-12-5 | | 5 |
| A0170-12-8 | | 8 |
| A0170-12-8 | | 8 |
| A0170-12-10 | | 10 |

The physico-chemical characteristics of the formulations were evaluated using analytical methods for viscosity, surface activity, zeta potential, and aerosol output rate.

Rheometry for Apparent Viscosity. The apparent viscosity was measured using a Rheometer (AR1000, TA Instruments, Newcastle, Del.). An aliquot (~400 µl) was analyzed using a step flow program as follows:

Conditioning step: Allow temperature to reach 25° C.

Step Flow 1: Linear ramp as 1/sec, 0 to 200 sec with 15 data point collection

Step Flow 2: Linear ramp as 1/sec, 200 to 0 sec with 15 data point collection

The viscosity value at the shear rate 157.2 $sec^{-1}$ from both the steps was recorded and the average of these two values is reported here.

Pulsating Bubble Surfactometry (PBS) for surface activity. The surface activity of the formulations was measured using a Pulsating Bubble Surfactometer (PBS, Electronetics Corporation, Amherst, N.Y.) at an oscillation frequency of 20 cycles/min, 5 mins read time at 37° C. The minimum surface tension values were determined for the samples at 3 mg/ml concentrations prior to aerosolization. The samples were diluted to 3 mg/ml TPL in 20 mM Tris-Ac buffer with 130 mM NaCl. The samples were aerosolized prior to the PBS measurement.

Aerosol output rate measurements. An Aeroneb Pro nebulizer was used to aerosolize the samples. This nebulizer uses vibrating mesh technology (with an aperture size of 4.8 microns) to generate the aerosol with a frequency of 128 KHz. All output rates were calculated through gravimetric analysis, and are averaged over a two-minute period of operation. Two sets of measurements were made with each sample. Operation at elevated temperatures was achieved using a heating tape which was tightly wrapped around the outside of the nebulizer. The heating tape was operated at 10% on-time, and the equipment was pre-heated 7 minutes before aerosolization. To avoid material losses to evaporation during pre-heating, the rubber filler plug for the nebulizer reservoir was closed until operation began. Aerosol collection was accomplished using a centrifuge tube that was placed at the output end of the nebulizer and submerged in an ice bath.

The surface activity of each formulation lot was evaluated by recording the minimum surface tension values of pre-aerosolized formulation samples. These samples were measured using PBS at a concentration of 3 mg/ml, as per the internal release assay.

The pre-aerosolization minimum surface tensions measured at 3 mg/ml by PBS are shown in FIG. 1. FIG. 1 shows that all DPPG formulations exhibit minimum surface tensions less than 10 mN/m and, moreover, these values are essentially indistinguishable from each other in this assay.

Figure 2:
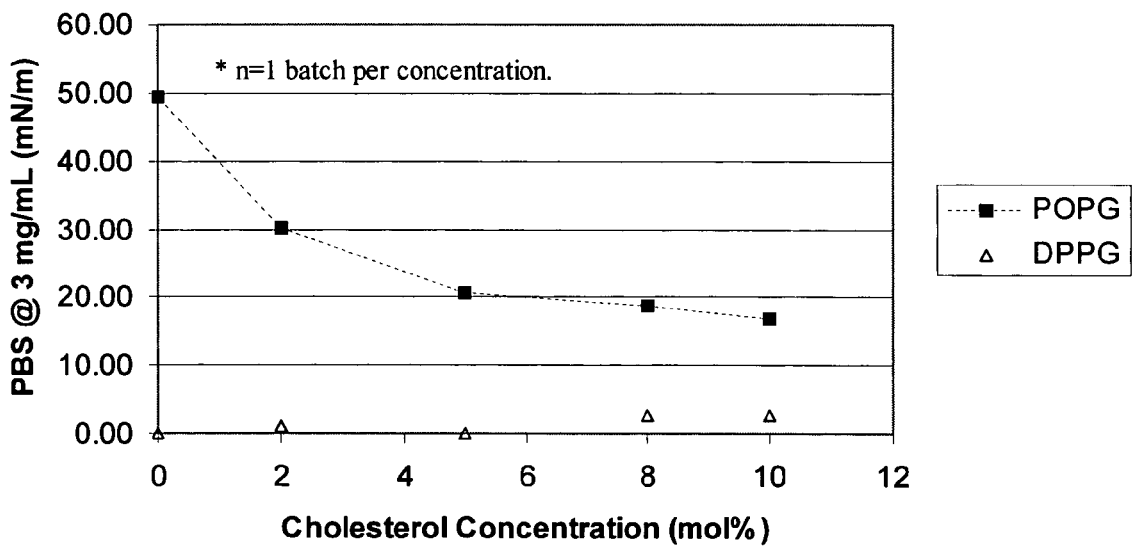
FIG. 2. Surface activities of formulations measured at 3 mg/ml TPL

FIG. 2 shows the comparison between the surface tension of DPPG formulations and POPG formulations containing cholesterol up to 10 mol % but lacking palmitic acid. FIG. 2 shows that all DPPG formulations exhibit minimum surface tensions of less than 3 mN/m. In contrast, formulations containing POPG and cholesterol all failed to demonstrate minimum surface tension values of less than 10 mN/m.

Figure 3:
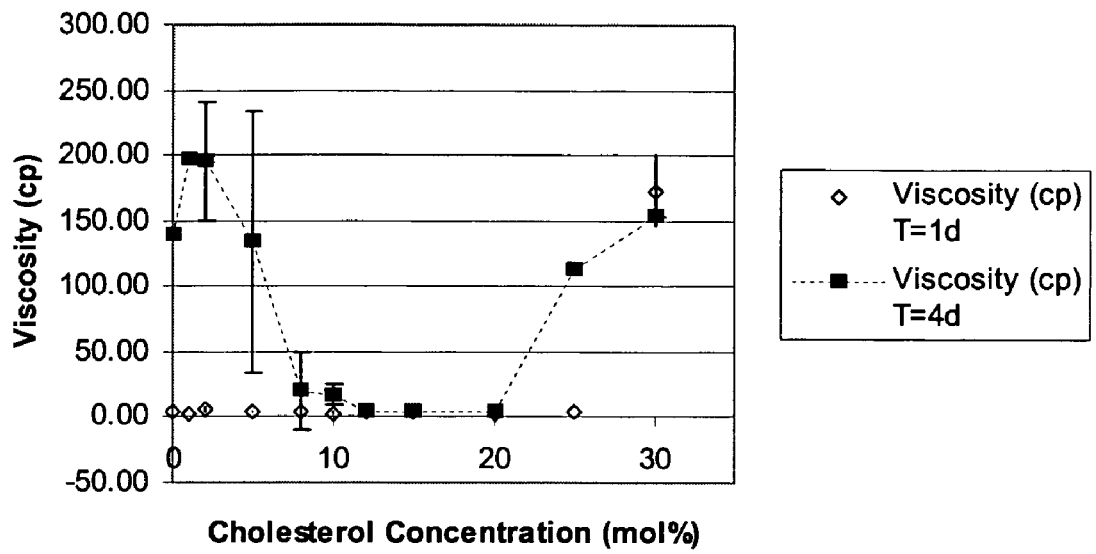
FIG. 3. Plot of cholesterol concentration vs. apparent viscosity for formulations after 1 and 4 days refrigerated storage.

The apparent viscosities of the DPPG formulation are plotted in FIG. 3 for both days 1 and 4 post hydration. FIG. 3 shows that all DPPG-cholesterol formulations up to 25 mol % cholesterol showed very low viscosity (less than 6 cp) one day after hydration with the exception of 30 mol % cholesterol formulations having higher viscosity (160 cp). 4 days after hydration, the viscosity of the formulations containing 0-10 mole % and 20-30 mole % cholesterol increased significantly. The viscosity of 0-10 mole % cholesterol formulations decreased substantially as the content of cholesterol was increased ranging from about 10-200 cp. Formulations containing 12-20 mole % cholesterol show no increase in viscosity and remained lower then 5 cp, while the viscosity of formulations in the range of 25-30 mole % cholesterol started to increase again up to 160 cp.

Figure 4:
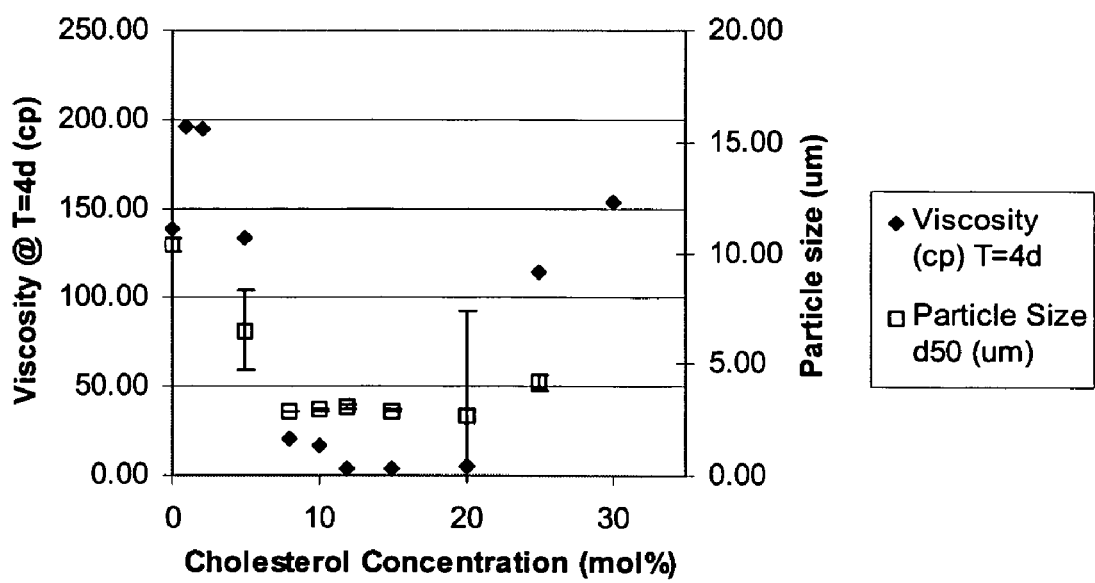
FIG. 4. Particle size analysis. Ten measurements of the volume median diameter (D50) were made and averaged for each formulation lot. The average of the D50's for the lots of each formulation are shown, along with the standard deviations. To show the correlation to viscosity, the viscosity 4 days post hydration was plotted as well.

The results of the particle size analyses performed on the liquid-dispersion formulations are shown in FIG. 4. The apparent viscosities of the formulations, 4 days post hydration, trend in a similar direction with particle size, with higher apparent viscosities observed for formulations having greater particle size.

Figure 5:
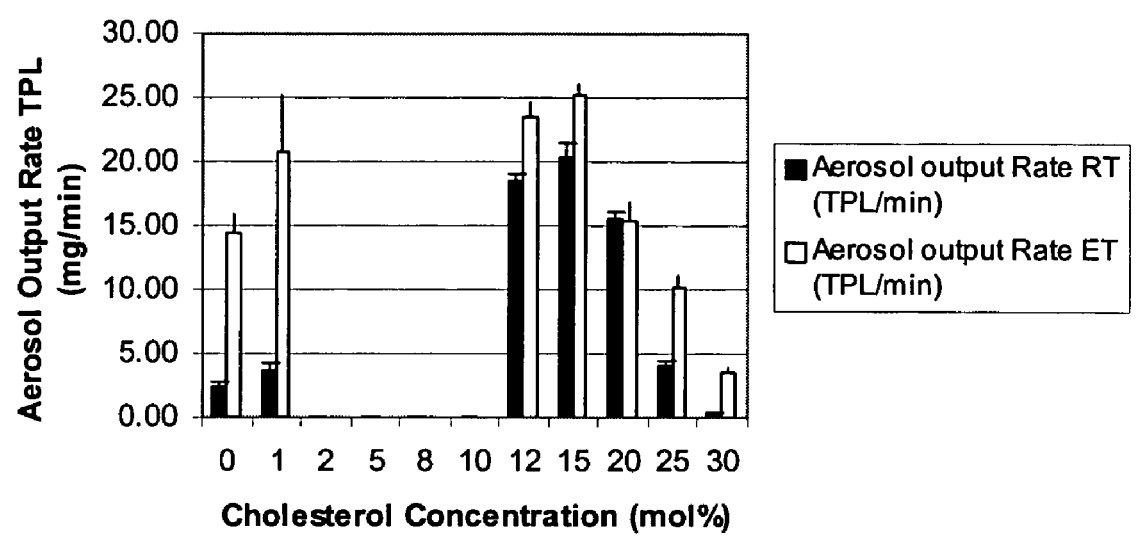

Aerosol output rates were measured at room temperature and elevated temperature (40-45° C. The aerosol output rates for the 60 mg/ml formulations are shown in FIG. 5 (mg-TPL/min). Values presented represent averages for each formulation type, with various individual lots produced (n=1-5) and tested for each formulation type and two or more measurements made for each lot. FIG. 5 shows that the output rates at RT of the test formulations are strongly influenced by the cholesterol content. The aerosolization rate increased with increasing cholesterol content up to 15 mol % and then decreases again with increasing cholesterol content up to 30 mol %. This trend was observed for formulations tested at 60 mg/ml concentration. The aerosolization rates at ET were about the same level (20-25 TPL mg/min) up to 20 mol % content of cholesterol and then decreased with increasing cholesterol content. The capability of these formulations to be aerosolized at RT with an output rate close to 20 mg/min has potential benefit over current $KL_4$-formulations. The increased content of cholesterol in DPPG formulations lacking palmitic acid were active pre-aerosolization exhibiting <the 10 mN/m minimum surface tension values when tested at 3 mg/ml TPL. All cholesterol formulations containing POPG exhibited poor minimum surface tension values. All cholesterol formulations prepared at 60 mg/ml TPL exhibited higher aerosol output rates than Surfaxin® tested at 30 mg/mL.

Example 2

Development of Novel Lung Surfactant Formulation Containing DPPG and Cholesterol-II Formulation of Lung Surfactant. Lab-scale formulations were prepared at 60 mg/ml (TPL) according to DOP-017, with the appropriate changes for cholesterol content variations described below (Table 4). Each formulation was prepared in formulation was prepared in triplicate (see lot numbers and names in Table 4) and individually characterized.

TABLE 4

Formulation Lot Numbers, Names, and Cholesterol Target Concentrations

| Formulation Lot | | Cholesterol | Concentration |
|---|---|---|---|
| Name | Number | mol (%) | mg/mL |
| 2Ch1 | A0170-14-2Ch1 | 2 | 0.32 |
| 2Ch2 | A0170-14-2Ch2 | 2 | 0.32 |
| 2Ch3 | A0170-14-2Ch3 | 2 | 0.32 |
| 8Ch1 | A0170-15-8Ch1 | 8 | 1.26 |
| 8Ch2 | A0170-15-8Ch2 | 8 | 1.26 |
| 8Ch3 | A0170-15-8Ch3 | 8 | 1.26 |
| 10Ch1 | A0170-14-10Ch1 | 10 | 1.58 |
| 10Ch2 | A0170-14-10Ch2 | 10 | 1.58 |
| 10Ch3 | A0170-14-10Ch3 | 10 | 1.58 |
| 12Ch1 | A0174-7-12Ch1 | 12 | 1.89 |
| 12Ch2 | A0174-7-12Ch2 | 12 | 1.89 |
| 12Ch3 | A0174-7-12Ch3 | 12 | 1.89 |
| 15Ch1 | A0174-7-15Ch1 | 15 | 2.36 |
| 15Ch2 | A0174-7-15Ch2 | 15 | 2.36 |
| 15Ch3 | A0174-7-15Ch3 | 15 | 2.36 |

Analytical assays and procedures that were used to characterize the formulations are summarized in Table 5. Each formulation was independently assayed.

The PBS activity measurements were made using a dilution-until-failure approach. That is, each formulation was diluted to 10 mg/ml TPL and analyzed by PBS. If the steady-state minimum surface tension did not meet an arbitrary failure criterium of, >10 mN/m, then the formulation was diluted 2× and the assay was repeated. This process was repeated until the formulation lot was sufficiently dilute to fail the >10 mN/m criterium. Triplicate measurements for each formulation were made at the lowest dilutions (i.e., the concentration at which the failure criterion was met for the average of the triplicate measurements). PBS activity was measured singularly at the 3 mg/ml formulation concentration.

TABLE 5

Summary of Assays Performed

| Assay |
| --- |
| 1. Surface activity by PBS |
| 2. Viscosity |
| 3. Particle size (dispersion) |
| 4. DPPC content by HPLC |
| 5. DPPG content by HPLC |
| 6. Cholesterol content by HPLC |
| 7. KL4 content by HPLC |

The surface activity of each formulation lot was evaluated by two means: 1) minimum surface tensions of formulation samples were measured using PBS at a concentration of 3 mg/ml, and 2) the failure concentration was measured on formulation samples. The second assay was designed to identify potential differences in activity of the formulation lots.

The minimum surface tensions measured at 3 mg/ml by PBS are shown in Table 6 (i.e., average (+/−standard deviation) of the three lots of each formulation). Table 6 shows that all formulations exhibit surface tension values of less than 10 mN/m when measured 7 or 14 days post hydration, and, moreover, these values are essentially indistinguishable from each other and from Surfaxin® measured in this assay at 10 mg/mL.

TABLE 6

Surface activities of formulations measured at 3 mg/ml TPL

| Formulation Name | Minimum Surface Tension* (mN/m) | | |
| --- | --- | --- | --- |
| | Day 1 | Day 7 | Day 14 |
| 2Ch | 5.6 ± 4.8 | 0.0 ± 0.0 | 0.0 ± 0.0 |
| 8Ch | 4.2 ± 2.6 | 0.0 ± 0.0 | 1.1 ± .7 |
| 10Ch | 7.2 ± 6.0 | 1.3 ± 1.4 | 2.8 ± 2.6 |
| 12 Ch | 13.6 ± 16.8 | 0.9 ± 1.3 | 0.0 ± 0.0 |
| 15 Ch | 15.8 ± 17.0 | 3.2 ± 2.8 | 0.8 ± 1.3 |
| Surfaxin ® | | | 0.0 ± 0.0 |

*Average of measurements for the three lots of each formulation

The "failure" concentrations for the individual formulation lots are listed in Table 7.

The failure concentration of Surfaxin® was 1.25 mg/ml. In general, the failure concentrations for the three lots of a given formulation type (i.e., 2Ch1, 2Ch2, and 2Ch3) were either all the same value or all within one dilution, as shown in Table 4, demonstrating reasonable consistency between the triplicate formulation lots. All formulations also demonstrate similar surface activity.

TABLE 7

Failure concentrations* of individual formulation lots measured by PBS after 2 weeks storage

| Formulation Name | Failure Concentration (mg/mL) |
| --- | --- |
| 2Ch1 | 0.625 |
| 2Ch2 | 0.625 |
| 2Ch3 | 0.625 |
| 8Ch1 | 1.25 |
| 8Ch2 | 1.25 |
| 8Ch3 | 1.25 |
| 10Ch1 | 1.25 |
| 10Ch2 | 0.625 |
| 10Ch3 | 0.625 |
| 12Ch1 | 0.625 |

TABLE 7-continued

Failure concentrations* of individual formulation lots measured by PBS after 2 weeks storage

| Formulation Name | Failure Concentration (mg/mL) |
| --- | --- |
| 12Ch2 | 0.625 |
| 12Ch3 | 0.3125 |
| 15Ch1 | 1.25 |
| 15Ch2 | 0.625 |
| 15Ch3 | 0.625 |

*Failure concentration is defined as the formulation concentration at which the average of triplicate PBS minimum surface tension measurements is greater than 10 mN/m.

Figure 6:
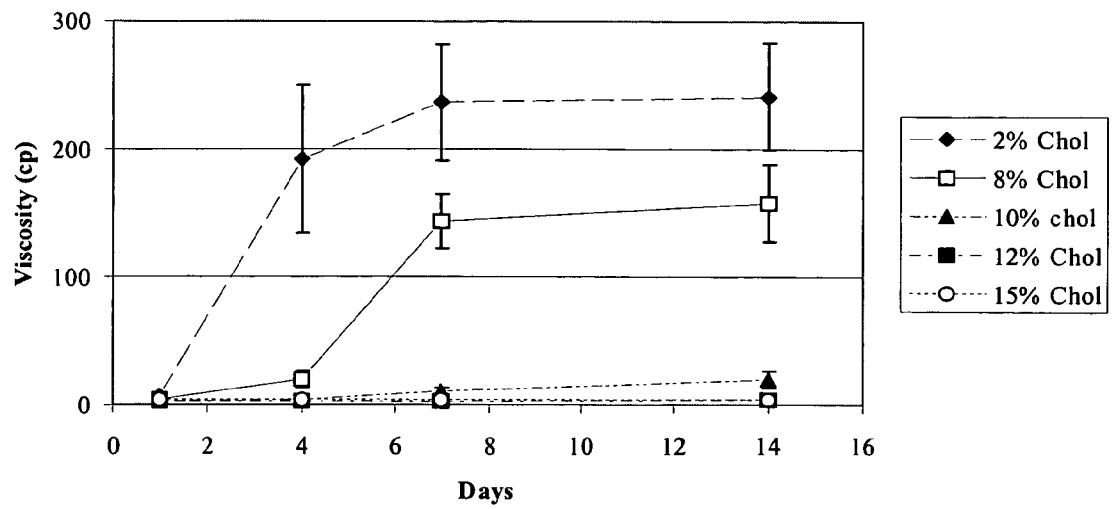
FIG. 6. Long-term apparent viscosity.

The apparent viscosities of the formulation are plotted in FIG. 6. FIG. 6 shows that all cholesterol formulations up to 15 mol % cholesterol showed very low viscosity (less than 6 cp) one day after hydration. However, during the first week post preparation, formulations containing up to 10 mol % (1.575 mg/mL) cholesterol showed an increase in viscosity that leveled off after 1 week. Nevertheless, formulations with 12 and 15 mol % cholesterol showed no increase in viscosity during the two weeks tested-period, and the viscosity remained below 4 cp.

Figure 7:
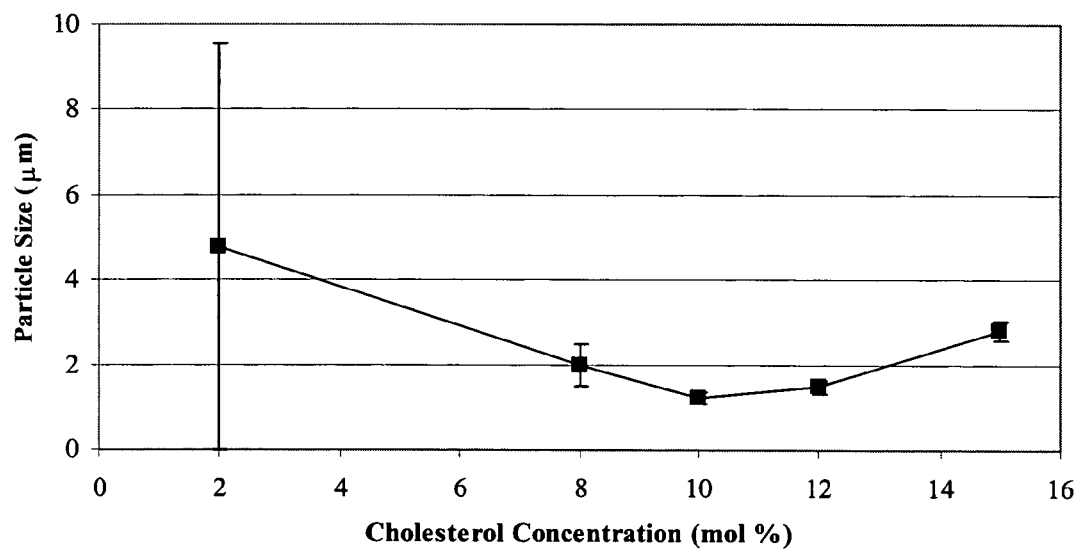
FIG. 7. Particle size analysis. Ten measurements of the volume median diameter (D50) were made and averaged for each formulation lot. The average of the D50's for the three lots of each formulation are shown, along with the standard deviations. Little to no difference in apparent particle size was observed, with the exception of the 2 mol % cholesterol formulations that exhibited larger apparent particle sizes at this 60 mg/ml concentration.

The results of the particle size analyses performed on the liquid-dispersion formulations are shown in FIG. 7. No significant trends were observed with the exception of the larger apparent particle sizes for the 2 mol % cholesterol formulation lots at this 60 mg/ml concentration, which also exhibit the highest viscosity after storage. Note that the measured median particle size for Surfaxin® using this method was 11.0 μm.

The results of the lipid and $KL_4$ HPLC assays on the 60 mg/ml formulations are shown in Table 8 Note that the target DPPC, POPG, and $KL_4$ concentrations for all of the formulations were 45, 15, and 1.60 mg/ml, respectively. The target concentrations for cholesterol are shown in Table 1. Table 8 shows that the measured lipid and peptide concentrations are in good agreement with the target values.

TABLE 8

DPPC, DPPG, Cholesterol and $KL_4$ concentrations of the formulations

| Name | | Concentration (mg/ml) | | | |
| --- | --- | --- | --- | --- | --- |
| | | DPPC | DPPG | Cholesterol | $KL_4$ |
| 2Ch | Ave: | 44.2 | 14.6 | ND | 1.6 |
| | Stdev. | 0.81 | 0.06 | | 0.08 |
| 8Ch | Ave: | 46.3 | 15.2 | 1.25 | 1.6 |
| | Stdev. | 2.40 | 0.27 | 0.02 | 0.06 |
| 10Ch | Ave: | 45.2 | 15.1 | 1.55 | 1.6 |
| | Stdev: | 2.15 | 0.35 | 0.04 | 0.06 |
| 12Ch | Ave: | 45.4 | 15.6 | 1.86 | 1.6 |
| | Stdev. | 1.42 | 0.12 | 0.03 | 0.01 |
| 15Ch | Ave: | 45.4 | 15.5 | 2.36 | 1.6 |
| | Stdev: | 0.06 | 0.07 | 0.03 | 0.02 |

Figure 8:
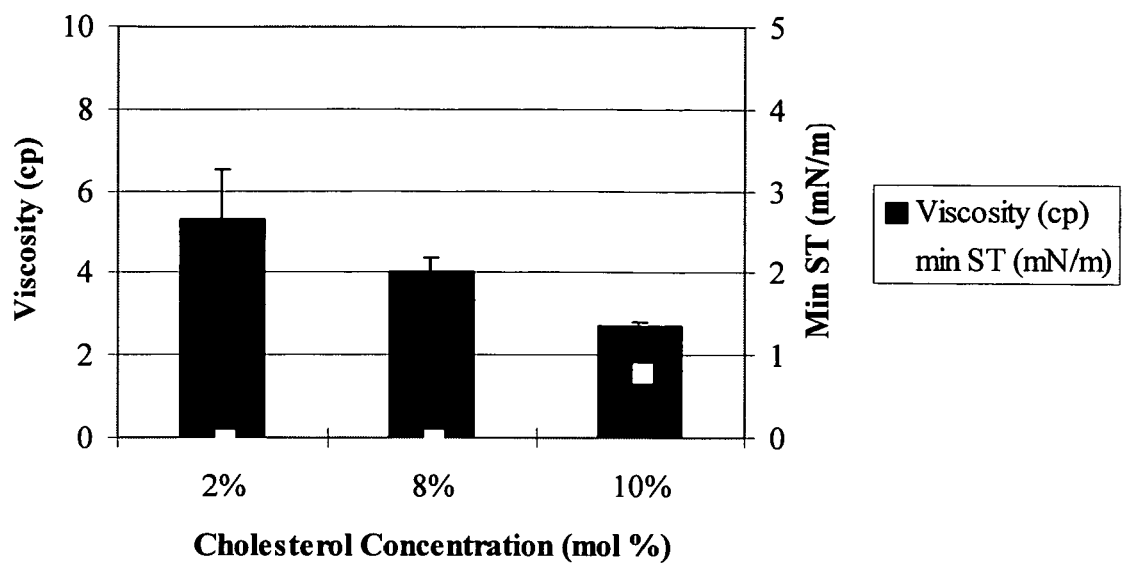
FIG. 8. Apparent viscosity and surface activity after 30 days at 25° C. and 60% humidity.

The stability results of the formulations in terms of apparent viscosity and surface activity after incubation at 25° C. and 60% relative humidity for 30 days are plotted in FIG. 8. FIG. 8 shows that in the period of 30 days, at 25° C. and 60% relative humidity there was no change in the initial viscosity of the formulations which remained below 6 cp, the formulations were still active in terms of surface activity (below 1 mN/m at 3 mg/mL) and there was no degradation of the formulations components as detected by HPLC.

Example 3

In Vivo Activity of a Cholesterol-Containing Composition

The change in the volume of the respiratory system is measured by placing an animal, in this case a pre-term rabbit, in a plethysmograph, and measuring the change in volume of gas into and out of the plethysmograph with a flow meter, or pneumotachograph. The stiffness of the respiratory system is calculated by dividing the tidal volume change by the airway pressure change during a mechanical breath. The parameter for this stiffness is the compliance of the respiratory system (Crs).

Figure 9:
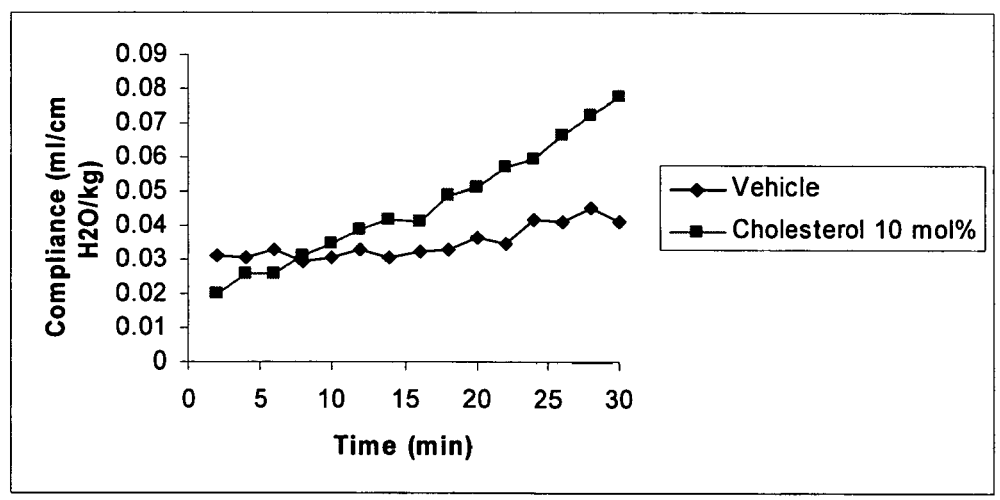
FIG. 9. The change in compliance of fetal rabbit lungs after treatment with a 30 mg/ml DPPC, DPPG and cholesterol (10 mol %) composition (n=6) compared with control animals treated with vehicle (n=6).

In surfactant-deficient fetal-rabbits treated with surfactant, Crs is expected to increase during mechanical ventilation, and reach a plateau in approximately 10-30 minutes. This increase is due to the spreading of the surfactant and the establishment of a surface-active lining of the alveoli. In surfactant-deficient animals, there can be a small increase in the Crs with mechanical ventilation due to the release of minimal stores of surfactant, but their lungs remain stiff because there is insufficient surfactant to prevent alveolar collapse with each exhalation. The expected course of Crs is shown in FIG. 9 for the mean Crs of six fetal rabbit pups treated with a 30 mg/ml DPPC, DPPG (3:1) and cholesterol (10 mole %) formulation and six control animals treated with vehicle (all at 27 days gestation) during 30 minutes of mechanical ventilation. The raw data is an average of 20 seconds worth of compliance data which is acquired every 2 minutes. Compliance values rise over time. The values for compliance are corrected for the weight of the pups. It can be seen that the cholesterol-containing formulation exhibits a positive trend toward improving compliance relative to a vehicle control.

Example 4

Development of Novel Lung Surfactant Formulations Containing No Palmitic Acid Formulation Details. All of the formulations prepared comprised of DPPC, POPG and $KL_4$ at ratios of 3 to 1 to 0.11 by weight respectively. The active components were dissolved in a 60% t-butanol (TBA) mixture (remaining 40% $H_2O$) such that the final total phospholipid concentration in the pre-lyo solvent system was 30 mg-TPL/ml. The TBA solution containing the actives was aliquoted into 20 mL serum vials at a fill volume of 9.1+/−0.1 mL and lyophilized using a developmental scale lyophilizer.

Reconstitution of samples. The lyophilized cakes were reconstituted by hand shaking using 20 mM Tris-Ac buffer at pH 7.6 containing 130 mM NaCl. The volume of buffer used for reconstitution was 4.3+/−0.1 ml resulting in a final concentration of 60 mgTPL/ml for the reconstituted samples. The samples were evaluated for apparent viscosity and in vitro surface activity upon reconstitution.

Apparent Viscosity Measurements. The apparent viscosities of the surfactant formulations were measured at a temperature of 25° C. using a TA AR1000 Rheometer (TA Instruments, New Castle, Del.) fitted with a 40 mm/10 acrylic cone. Approximately 350 µL of undiluted surfactant was placed on the rheometer and allowed to thermally equilibrate at 25° C. A step flow procedure was utilized to analyze the samples with a linear increase in the shear rate with time (0 to 200 $sec^{-1}$) followed by linear decrease in shear rate (200 to 0 $sec^{-1}$). During each ramp up and ramp down process, 15 points were collected resulting in approximately 6 minutes of total run time. The viscosities measured at a shear rate of 157 $sec^{-1}$ during the ramp up and ramp down were averaged and reported as the apparent viscosity for each sample.

In vitro activity measurements using the PBS. The surface activities of reconstituted formulations were measured at 3 mg-TPL/ml using a Pulsating Bubble Surfactometer (PBS, Electronetics Corp, Seminole, Fla.). The samples were diluted in 20 mM Tris-Ac buffer at pH 7.6 containing 130 mM NaCl. Upon dilution, the samples were vortexed for 10 seconds and heated in a 37° C. water bath for 10 minutes. After removal from the water bath, the samples were vortexed for 10 seconds. Approximately 50 µL of sample was then analyzed on the PBS at 37° C. A bubble was formed by the user and allowed to equilibrate for 1 minute. The bubble was then pulsated at an oscillation frequency of 20 cycles/min for 6 minutes, during which time the bubble cycled from a minimum radius of 0.4 mm to a maximum radius of 0.55 mm. The pressure transducer in the PBS instrument measures a pressure, which is used to calculate the surface tension using the Laplace equation. The surface tension after 100 cycles was determined and reported as the minimum surface tension of the sample.

Results. The apparent viscosities and in vitro activities for the formulations tested are represented in Table 9. The data presented in the table shows that the minimum surface tension of all the formulations were <15 mN/m.

TABLE 9

Apparent Viscosities and in vitro activities of formulations studied

| Sample ID | Component Name | # Samples | Viscosity 60 mg/ml (cp) | Min ST @ 3 mg/ml (mN/m) |
|---|---|---|---|---|
| Control | Palmitic Acid | 15 | 82 +/− 27 | 0 |
| 2-MeP | Methyl Palmitate | 10 | 16 +/− 2 | 0 +/− 0 |
| 2-EtP | Ethyl Palmitate | 1 | 13 | 9 |
| 2-IpP | Isopropyl Palmitate | 1 | 19 | 13 |
| 2-ChP | Cholesteryl Palmitate | 1 | 39 | 0 |
| 2-PaP | Palmitoyl Palmitate | 1 | 157 | 10 |
| 2-NaP | Sodium Palmitate | 1 | 229 | 0 |
| 2-KP | Potassium Palmitate | 1 | 162 | 0 |
| 2-TPT | Tripalmitin | 1 | 91 | 0 |
| 2-0PaCh | Cholesterol | 1 | 57 | 13 |
| 4C | Cetyl Alcohol | 10 | 45 +/− 7 | 2 +/− 5 |

Example 5

Development of Novel Lung Surfactant Formulations Containing No POPG (Palmitoyloleoyl Phosphatidylglycerol)

Formulation Details. All of the formulations prepared comprised of DPPC, PA and $KL_4$ at ratios of 3 to 0.54 to 0.11 by weight respectively. The active components were dissolved in a 60% t-butanol (TBA) mixture (remaining 40% $H_2O$) such that the final total phospholipid concentration in the pre-lyo solvent system was 30 mg-TPL/ml. The TBA solution containing the actives was aliquoted into 20 mL serum vials at a fill volume of 9.1+/−0.1 mL and lyophilized using a developmental scale lyophilizer.

Reconstitution of samples. The lyophilized cakes were reconstituted by hand shaking using 20 mM Tris-Ac buffer at pH 7.6 containing 130 mM NaCl. The volume of buffer used for reconstitution was 4.3+/−0.1 ml resulting in a final concentration of 60 mgTPL/ml for the reconstituted samples. The samples were evaluated for apparent viscosity and in vitro surface activity upon reconstitution.

Apparent Viscosity Measurements. As described above in Example 4.

In vitro activity measurements using the PBS. As described above in Example 4.

Results. The apparent viscosities and in vitro activities for the formulations tested are represented in Table 10. The data presented in the table shows that the minimum surface tension of all the formulations were <15 mN/m. Additionally, the replacement of POPG in the formulation with other lipids (both neutral and charged) resulted in reduced apparent viscosities of the formulation.

system was 30 mg-TPL/ml. The TBA solution containing the actives was aliquoted into 20 mL serum vials at a fill volume of 9.1+/−0.1 mL and lyophilized using a developmental scale lyophilizer.

Reconstitution of samples. The lyophilized cakes were reconstituted by hand shaking using 20 mM Tris-Ac buffer at pH 7.6 containing 130 mM NaCl. The volume of buffer used for reconstitution was 4.3+/−0.1 ml resulting in a final concentration of 60 mgTPL/ml for the reconstituted samples. The samples were evaluated for apparent viscosity and in vitro surface activity upon reconstitution.

Apparent Viscosity Measurement. As described above in Example 4.

TABLE 10

Apparent Viscosities and in vitro activities of formulations studied

| Sample ID | Component Name | # Samples | Viscosity 60 mg/ml (cp) | Min ST @ 3 mg/ml (mN/m) |
|---|---|---|---|---|
| Control | POPG | 15 | 82 +/− 27 | 0 |
| 3-DSPC | Di-stearoyl phosphatidylcholine | 7 | 33 +/− 5 | 2 +/− 2 |
| 3-DSPE | Di-stearoyl phosphatidylethanolamine | 1 | 41.9 | 0 |
| 3-POPC | Palmitoyl Oleoyl Phosphatidylcholine | 7 | 19 +/− 5 | 1.2 |
| 3-POPE | Palmitoyl Oleoyl Phosphatidylethanolamine | 1 | 54.2 | 0 |
| 3-PPoPC | Palmitoyl Palmito-oeloyl Phosphatidylcholine | 4 | 17 +/− 10 | 0 |
| 3-DMPC | Di-myristoyl phosphatidylcholine | 7 | 27 +/− 5 | 3 +/− 4 |
| 3-DMPE | Di-myristoyl phosphatidylethanolamine | 1 | 62 | 1 |
| 3-POPS | Palmitoyl Oleoyl Phosphatidylserine | 1 | 76 | 0 |
| 3-DMPG | Di-myristoyl phosphatidylglycerol | 1 | 21.3 | 0 |
| 3-DPPG | Di-palmitoyl phosphatidylglycerol | 1 | 43.5 | 0 |
| 3-DPPE | Di-palmitoyl phosphatidylethanolamine | 1 | 64.5 | 2.5 |

Example 6

Development of Novel Lung Surfactant Formulations Containing No POPG (Palmitoyloleoyl Phosphatidylglycerol) and No Palmitic Acid Formulation Details. All of the formulations prepared comprised of DPPC and KL$_4$ at ratios of 3 to 0.11 by weight respectively. The active components were dissolved in a 60% t-butanol (TBA) mixture (remaining 40% H$_2$O) such that the final total phospholipid concentration in the pre-lyo solvent In vitro activity measurements using the PBS. As described above in Example 4.

Results. The apparent viscosities and in vitro activities for the formulations tested are represented in Table 11. The data presented in the table shows that the minimum surface tension of all the formulations were <15 mN/m. Additionally, the replacement of POPG and palmitic acid in the formulations with alternate lipids/esters resulted in lower apparent viscosities of the samples.

TABLE 11

Apparent Viscosities and in vitro activities of formulations studied

| Sample ID | Replacement Component for PA | Replacement Component for POPG | # Samples | Viscosity 60 mg/ml (cp) | Min ST @ 3 mg/ml (mN/m) |
|---|---|---|---|---|---|
| Control | Palmitic Acid | POPG | 15 | 82 +/− 27 | 0 |
| 5-CH-2 | Cholesterol | DPPG | 1 | 33.2 | 0.4 |
| 5-CH-5 | Cholesterol | DPPG | 1 | 33.6 | 5.5 |
| 5-CH-8 | Cholesterol | DPPG | 1 | 39.3 | 0.8 |
| 5-CH-10 | Cholesterol | DPPG | 4 | 51 +/− 12 | 0.3 +/− 0.6 |
| 5-CH-12 | Cholesterol | DPPG | 1 | 36.1 | 0 |
| 5-CH-15 | Cholesterol | DPPG | 1 | 42.6 | 3.8 |
| 5-VE-1 | Vitamin E | DPPG | 1 | 22.4 | 0 |
| 5-VE-5 | Vitamin E | DPPG | 1 | 34.5 | 0 |
| 5-VE-10 | Vitamin E | DPPG | 1 | 26.7 | 0 |
| 5-VE-15 | Vitamin E | DPPG | 1 | 32.7 | 0 |
| 5-VE-20 | Vitamin E | DPPG | 1 | 24.6 | 0 |
| 3-POPC-2 | Methyl Palmitate | POPC | 3 | 16 +/− 2 | 5 +/− 9 |
| 3-POPC-3 | Cetyl Alcohol | POPC | 3 | 12 +/− 0.8 | 8 +/− 4 |
| 3-DMPC-2 | Methyl Palmitate | DMPC | 3 | 37 +/− 1.9 | 0 +/− 0 |
| 3-DMPC-3 | Cetyl Alcohol | DMPC | 3 | 20 +/− 3.8 | 5 +/− 7.9 |
| 3-DSPC-2 | Methyl Palmitate | DSPC | 3 | 51 +/− 3.2 | 1 +/− 2.4 |
| 3-DSPC-3 | Cetyl Alcohol | DSPC | 3 | 40 +/− 4 | 1 +/− 0.6 |

Example 7

Improved Thermal Stability of a Formulation Containing No Palmitic Acid and No POPG Formulation Details. Two formulations were prepared. One formulation comprised of DPPC/POPG/Palmitic Acid/KL$_4$ at ratios of 3/1/0.54/0.11 by weight respectively, was prepared at a total phospholipid concentration of 30 mg-TPL/ml. The second formulation comprised of DPPC/DPPG/Cholesterol/KL$_4$ at ratios of 3/1/1.9/0.11 by weight and prepared at a total phospholipid concentration of 60 mg-TPL/ml. The samples were prepared by the rotary evaporation process as described in Example 4.

Stability Study. The samples prepared above were aliquoted into 10 ml vials at a fill volume of 8 mls. The formulations were stored under three different conditions as below and tested over time at 0, 7, 14, 30, 60, 90 and 180 days.
1. Storage at 5° C.±3° C., ambient RH
2. Storage at 25° C.±3° C., 60% RH
3. Storage at 40° C.±3° C., 75% RH Thermal stability, which is equivalent to accelerated (thermal) storage stability testing, was designed to determine enhanced storage stability.

The analytical testing included measurements of apparent viscosity, in vitro surface activity, KL$_4$ concentration using RP-HPLC and aerosol output rate.

Apparent Viscosity Measurements. The apparent viscosity measurements were performed as described in Example 4.

In vitro activity measurements using the PBS. The surface activities of reconstituted formulations were measured using dilution curves using a Pulsating Bubble Surfactometer (PBS, Electronetics Corp, Seminole, Fla.). The samples were initially diluted to 10 mg-TPL/ml followed by doubling dilutions until the minimum surface tension at 100 cycles was >10 mN/m (this concentration is referred to as the failure concentration for the sample). The surface tension at this dilution and one prior dilution were then measured two more times. The key readouts for the samples included the failure concentration and the minimum surface tension at 10 mg-TPL/ml. The measurement details for the PBS are described in Example 4.

Aerosol output rate measurements. An Aeroneb Pro nebulizer was used to aerosolize the samples. This nebulizer uses vibrating mesh technology (with an aperture size of 4.8 microns) to generate the aerosol with a frequency of 128 KHz. All output rates were calculated through gravimetric analysis, and are averaged over a two-minute period of operation. Two sets of measurements were made with each sample. Operation at elevated temperatures was achieved using a heating tape which was tightly wrapped around the outside of the nebulizer. The heating tape was operated at 10% on-time, and the equipment was pre-heated 7 minutes before aerosolization. To avoid material losses to evaporation during pre-heating, the rubber filler plug for the nebulizer reservoir was closed until operation began.

Measurement of KL$_4$ concentration using RP-HPLC. Approximately 250 mg of the sample was weighed in a 15 ml eppendorf tubes and 1 ml of TFA was added to the sample. Upon dissolution of the sample in TFA, 10 ml of a 1:1 solution of H$_2$O:ACN was added. The mixture was vortexed and then centrifuged at 3000 rpm for 20 min in order to pellet the lipids. A 250-ul aliquot of the supernatant was loaded onto the column. KL$_4$ analysis was carried out on a HP1100 (Agilent Technologies, Palo Alto, Calif.). A Zorbax-SB, C-18, 5μ, 4.6×250 mm (Agilent Technologies, Palo Alto, Calif.) was used for the analysis. The eluent system comprised of a gradient of H$_2$O and ACN with TFA as a modifier (details provided below) at a flow rate of 1 mL/min. The column was maintained at 60° C. with UV signal detection at 214 nm. The running buffers were 60% H$_2$O, 40% ACN, 0.1% TFA (Solvent A) and 90% ACN, 10% H$_2$O, 0.1% TFA (Solvent B). The eluent system was 0% B over 10 min, 0-100% B in 10 mins, 100% B for 10 mins; 100-0% B in 1 min and 0% B for 4 min.

Results

Figure 10:
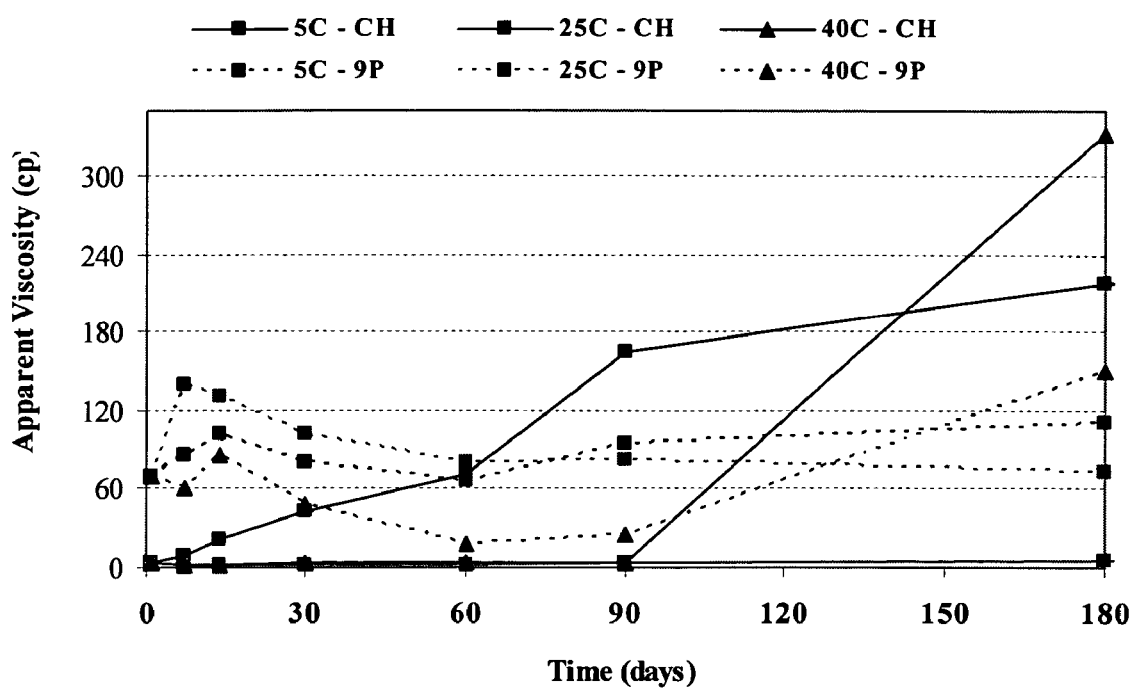
FIG. 10. Apparent viscosity data for formulations placed on thermal stability.

Apparent Viscosity. The apparent viscosity of the formulations is depicted in FIG. 10. The data indicates that the apparent viscosity for the cholesterol (CH) containing formulation does not change at 25° C. up to 180 days of storage. An increase in viscosity is observed for the cholesterol containing formulation at 5° C.

In vitro Surface Activity. The in vitro surface activity data for the samples is presented in Table 12. The data indicates that the failure concentrations of both control (9P) and CH formulations noisy. The failure concentrations for the cholesterol formulations are greater than the palmitic acid containing formulations at higher storage temperatures.

TABLE 12

In vitro surface activity data for formulations placed on thermal stability

| A0174-040 (9P) | | | | Min ST @ 10 mg/ml (9P) | | | |
|---|---|---|---|---|---|---|---|
| Time | Failure Conc (mg/ml) | | | Time | Min ST (mN/m) | | |
| (days) | 5° C. | 25° C. | 40° C. | (days) | 5° C. | 25° C. | 40° C. |
| 0 | | 5 | | 0 | | 0.00 | |
| 7 | 1.25 | 0.625 | 1.3 | 7 | 0.00 | 3.8 | 0.0 |
| 14 | 1.25 | 1.25 | 0.625 | 14 | 0.0 | 3.6 | 5.1 |
| 30 | 0.625 | 0.3125 | 2.5 | 30 | 0.0 | 0.4 | 3.9 |
| 60 | 0.625 | <0.625 | 0.625 | 60 | 0 | 1.2 | 0 |
| 90 | <0.625 | <0.625 | <0.625 | 90 | 0 | 0.4 | 0.4 |
| 180 | 0.3125 | <1.25 | <1.25 | 180 | 0 | 0 | 0 |

| A0174-038 (12% CH) | | | | Min ST @ 10 mg/ml (12% CH) | | | |
|---|---|---|---|---|---|---|---|
| Time | Failure Conc (mg/ml) | | | Time | Min ST (mN/m) | | |
| (days) | 5° C. | 25° C. | 40° C. | (days) | 5° C. | 25° C. | 40° C. |
| 0 | | 10 | | 0 | | 7.7 | |
| 7 | 2.5 | 10 | 5 | 7 | 7.7 | 14.4 | 2.7 |
| 14 | 5 | 5 | 10 | 14 | 0.8 | 2.7 | 10.6 |
| 30 | 0.63 | 1.25 | 1.25 | 30 | 0.0 | 0.8 | 1.6 |
| 60 | 1.25 | 1.25 | 1.25 | 60 | 0 | 0 | 0 |
| 90 | 0.625 | 1.25 | 2.5 | 90 | 0 | 0.8 | 0 |
| 180 | 0.625 | 1.25 | 10 | 180 | 0.4 | 0 | 16.6 |

Figure 11:
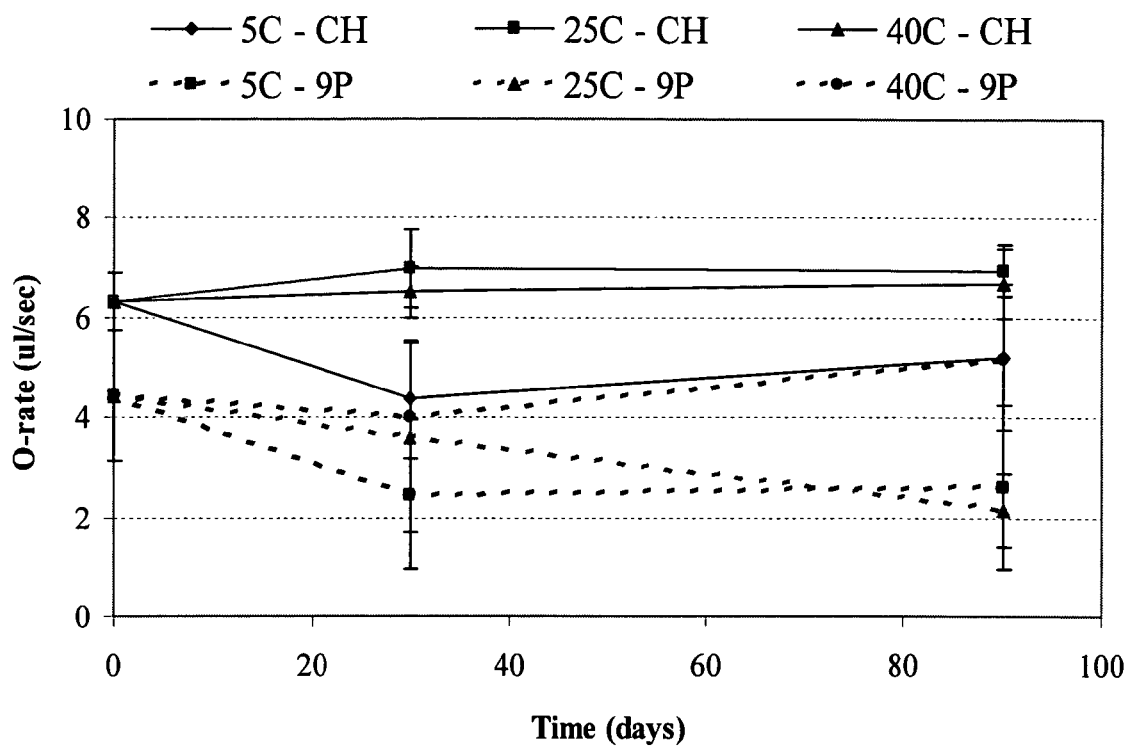
FIG. 11. Aerosol output rate measurements for formulations placed on thermal stability.

Aerosol Output Rate Measurements. The aerosol output rate measurements are depicted in FIG. 11. The data shows that the aerosol output rates for the cholesterol containing formulations are greater than those for the palmitic acid containing formulations at all storage temperatures and times.

Figure 12:
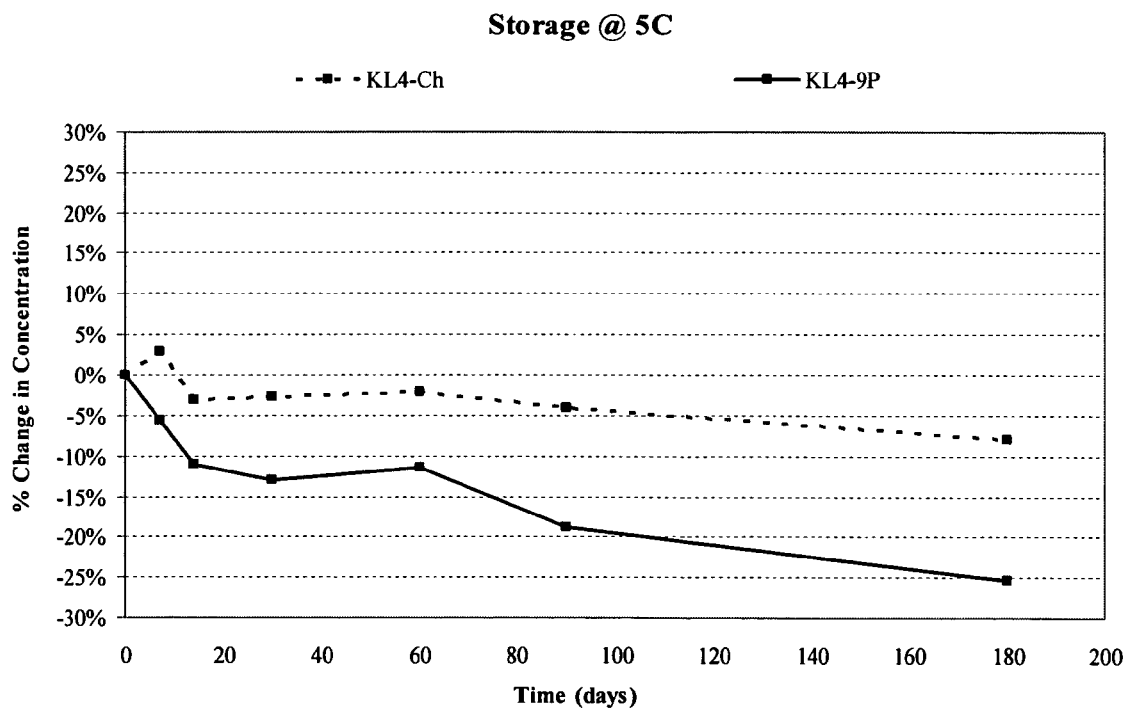
FIG. 12. Percent Loss of $KL_4$ for the formulations placed on thermal stability at 5° C. storage.
Figure 13:
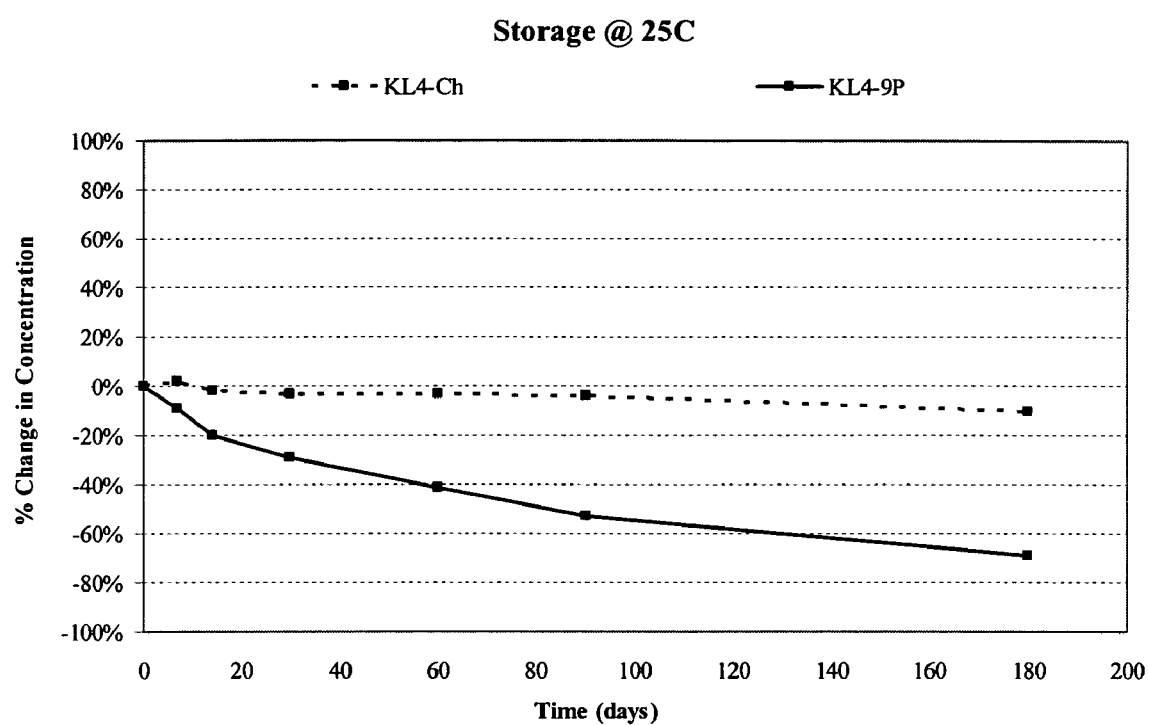
FIG. 13. Percent Loss of $KL_4$ for the formulations placed on thermal stability at 25° C. storage.

Change in the KL$_4$ concentration of the formulations over time. The change in the KL$_4$ concentrations for the samples containing cholestereol and palmitic acid stored at 5° C. and 25° C. are depicted in FIGS. 12 and 13 respectively. The data presented in the figures shows much improved thermal stability for the KL$_4$ in the cholesterol containing formulation when compared with the palmitic acid containing formulation. At 5° C., the % loss of KL$_4$ for the cholesterol containing formulation is 7.5% as compared to 25% for the palmitic acid formulation (a threefold improvement in the thermal stability for the cholesterol containing formulation). Similarly, FIG. 13 shows that the loss in KL$_4$ is 69% for the palmitic acid formulation as compared to 10% for the cholesterol containing formulation.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

Each recited range includes all combinations and sub-combinations of ranges, as well as specific numerals contained therein.

What is claimed is:

1. A biomimetic pulmonary surfactant comprising:
dipalmitoyl phosphatidylcholine,
phosphatidyl glycerol,
a synthetic surfactant polypeptide having at least 10 amino acid residues and no more than 60 amino acid residues, the synthetic surfactant polypeptide including a sequence having alternating hydrophobic and hydrophilic amino acid residue regions represented by the formula $(Z_aU_b)_cZ_d$, wherein: Z is a hydrophilic amino acid residue independently selected from the group consisting of R and K; U is a hydrophobic amino acid residue independently selected from the group consisting of L and C; a is 1 or 2; b has an average value of about 3 to about 8; c is 1 to 10; and d is 0 to 2, and essentially neutral lipid,
and having essentially no 1-palmitoyl 2-oleoyl phosphatidylglycerol and essentially no palmitic acid.

2. The pulmonary surfactant of claim 1, wherein the phosphatidylglycerol is saturated, non-saturated or semi-saturated.

3. The pulmonary surfactant of claim 2, wherein the saturated phosphatidylglycerol is dipalmitoyl phosphatidylglycerol.

4. The pulmonary surfactant of claim 1, wherein each of 1-palmitoyl 2-oleoyl phosphatidylglycerol and palmitic acid are present in an amount less than about five mole percent of total phospholipid.

5. The pulmonary surfactant of claim 1, wherein essentially neutral lipid comprises cholesterol.

6. The pulmonary surfactant of claim 1, wherein essentially neutral lipid comprises a fatty acid, a fatty acid ester, a fatty acid alcohol, cholesterol, corticosteroid, glucocorticosteroid, trifluorinate glucocorticoid, β2 agonist, plant sterol, phospholipid, phosphatidylcholine, phosphatidyl ethanolamine, phosphatidylinositol, sphingomyelin, diglycerides, diolein, dipalmitolein, mixed caprylin-caprin, triglycerides, triolein, tripalmitolein, trilinolein, tricaprylin, or trilaurin.

7. The pulmonary surfactant of claim 5, wherein the cholesterol concentration is from about 0.1 mol % to about 50 mol %.

8. The pulmonary surfactant of claim 5, wherein the cholesterol concentration is from about 1 mol % to about 20 mol %.

9. The pulmonary surfactant of claim 5, wherein the cholesterol concentration is cholesterol concentration from about 8 mol % to about 15 mol %.

10. The pulmonary surfactant of claim 3, wherein the molar ratio of dipalmitoyl phosphatidylcholine to dipalmitoyl phosphatidylglycerol is 4 to 1.

11. The pulmonary surfactant of claim 3, wherein the molar ratio of dipalmitoyl phosphatidylcholine to dipalmitoyl phosphatidylglycerol is 7 to 3.

12. The pulmonary surfactant of claim 3, wherein the molar ratio of dipalmitoyl phosphatidylcholine to dipalmitoyl phosphatidylglycerol is 3 to 1.

13. The pulmonary surfactant of claim 1, wherein the total concentration of dipalmitoyl phosphatidylcholine and phosphatidylglycerol is from about 10 mg/ml to about 150 mg/ml.

14. The pulmonary surfactant of claim 13, wherein the total concentration of dipalmitoyl phosphatidylcholine and phosphatidylglycerol is from about 50 mg/ml to about 125 mg/ml.

15. The pulmonary surfactant of claim 1, wherein a dynamic surface tension of the surfactant as measured by pulsating bubble surface tensiometry is 10 mN/m or less.

16. The pulmonary surfactant of claim 1, having an amino acid residue sequence represented by the formula: KLLLLKLLLLKLLLLKLLLLK (SEQ ID NO:1).

17. A biomimetic pulmonary surfactant consisting essentially of dipalmitoyl phosphatidylcholine, dipalmitoyl phosphatidylglycerol, essentially neutral lipid and synthetic surfactant polypeptide, wherein the synthetic surfactant polypeptide comprises at least 10 amino acid residues and no more than 60 amino acid residues, the polypeptide including a sequence having alternating hydrophobic and hydrophilic amino acid residue regions represented by the formula $(Z_aU_b)_cZ_d$, wherein: Z is a hydrophilic amino acid residue independently selected from the group consisting of R and K; U is a hydrophobic amino acid residue independently selected from the group consisting of L and C; a is 1 or 2; b has an average value of about 3 to about 8; c is 1 to 10; and d is 0 to 2.

18. The pulmonary surfactant of claim 17, wherein essentially neutral lipid is cholesterol.

19. The pulmonary surfactant of claim 17 wherein essentially neutral lipid comprises a fatty acid, a fatty acid ester, a fatty acid alcohol, cholesterol, corticosteroid, glucocorticosteroid, trifluorinate glucocorticoid, β2 agonist, plant sterol, phospholipid, phosphatidylcholine, phosphatidylethanolamine, phosphatidylinositol, sphingomyelin, diglycerides, fatty alcohols, diolein, dipalmitolein, mixed caprylin-caprin, triglycerides, triolein, tripalmitolein, trilinolein, tricaprylin, or trilaurin.

20. The pulmonary surfactant of claim 17, having an amino acid residue sequence represented by the formula: KLLLLKLLLLKLLLLKLLLLK (SEQ ID NO:1).

* * * * *

UNITED STATES PATENT AND TRADEMARK OFFICE
CERTIFICATE OF CORRECTION

| | | |
|---|---|---|
| PATENT NO. | : 8,337,815 B2 | Page 1 of 1 |
| APPLICATION NO. | : 11/316308 | |
| DATED | : December 25, 2012 | |
| INVENTOR(S) | : Rairkar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1195 days.

Signed and Sealed this
Sixteenth Day of December, 2014

Michelle K. Lee
*Deputy Director of the United States Patent and Trademark Office*

```
                        SEQUENCE LISTING

<160> NUMBER OF SEQ ID NOS: 15

<210> SEQ ID NO 1
<211> LENGTH: 21
<212> TYPE: PRT
<213> ORGANISM: Artificial Sequence
<220> FEATURE:
<223> OTHER INFORMATION: Synthetic Construct

<400> SEQUENCE: 1

Lys Leu Leu Leu Leu Lys Leu Leu Leu Leu Lys Leu Leu Leu Leu Lys
1               5                   10                  15

Leu Leu Leu Leu Lys
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Lys Leu Leu Leu Leu Leu Leu Leu Leu Lys Leu Leu Leu Leu Leu Leu
1               5                   10                  15

Leu Leu Lys Leu Leu
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

Lys Lys Leu Leu Leu Leu Leu Leu Lys Lys Leu Leu Leu Leu Leu Leu
1               5                   10                  15

Leu Leu Lys Lys Leu
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic Construct

<400> SEQUENCE: 4

Asp Leu Leu Leu Leu Asp Leu Leu Leu Leu Asp Leu Leu Leu Leu Asp
1               5                   10                  15

Leu Leu Leu Leu Asp
            20

<210> SEQ ID NO 5
```

```
<211> LENGTH: 21
<212> TYPE: PRT
<213> ORGANISM: Artificial Sequence
<220> FEATURE:
<223> OTHER INFORMATION: Synthetic Construct

<400> SEQUENCE: 5

Arg Leu Leu Leu Leu Arg Leu Leu Leu Arg Leu Leu Leu Leu Arg
1               5                   10                  15

Leu Leu Leu Leu Arg
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic Construct

<400> SEQUENCE: 6

Arg Leu Leu Leu Leu Leu Leu Leu Arg Leu Leu Leu Leu Leu Leu
1               5                   10                  15

Leu Leu Arg Leu Leu
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic Construct

<400> SEQUENCE: 7

Arg Arg Leu Leu Leu Leu Leu Leu Arg Arg Leu Leu Leu Leu Leu
1               5                   10                  15

Leu Leu Arg Arg Leu
            20

<210> SEQ ID NO 8
<211> LENGTH: 19
<212> TYPE: PRT
<213> ORGANISM: Artificial Sequence
<220> FEATURE:
<223> OTHER INFORMATION: Synthetic Construct

<400> SEQUENCE: 8

Arg Leu Leu Leu Leu Cys Leu Leu Leu Arg Leu Leu Leu Leu Cys Leu
1               5                   10                  15

Leu Leu Arg

<210> SEQ ID NO 9
<211> LENGTH: 21
<212> TYPE: PRT
<213> ORGANISM: Artificial Sequence
<220> FEATURE:
<223> OTHER INFORMATION: Synthetic Construct

<400> SEQUENCE: 9

Arg Leu Leu Leu Leu Cys Leu Leu Leu Arg Leu Leu Leu Leu Cys Leu
1               5                   10                  15

Leu Leu Arg Leu Leu
            20

<210> SEQ ID NO 10
<211> LENGTH: 28
```

```
<212> TYPE: PRT
<213> ORGANISM: Artificial Sequence
<220> FEATURE:
<223> OTHER INFORMATION: Synthetic Construct

<400> SEQUENCE: 10

Arg Leu Leu Leu Leu Cys Leu Leu Arg Leu Leu Leu Leu Cys Leu
1               5                   10                  15

Leu Leu Arg Leu Leu Leu Leu Cys Leu Leu Leu Arg
            20                  25

<210> SEQ ID NO 11
<211> LENGTH: 21
<212> TYPE: PRT
<213> ORGANISM: Artificial Sequence
<220> FEATURE:
<223> OTHER INFORMATION: Synthetic Construct

<400> SEQUENCE: 11

His Leu Leu Leu Leu His Leu Leu Leu His Leu Leu Leu Leu His
1               5                   10                  15

Leu Leu Leu Leu His
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic Construct

<400> SEQUENCE: 12

Arg Leu Leu Leu Leu Cys Leu Leu Arg Leu Leu Leu Leu Cys
1               5                   10                  15

Leu Leu Leu Arg
            20

<210> SEQ ID NO 13
<211> LENGTH: 22
<212> TYPE: PRT
<213> ORGANISM: Artificial Sequence
<220> FEATURE:
<223> OTHER INFORMATION: Synthetic Construct

<400> SEQUENCE: 13

Arg Leu Leu Leu Leu Leu Cys Leu Leu Leu Arg Leu Leu Leu Cys
1               5                   10                  15

Leu Leu Leu Arg Leu Leu
            20

<210> SEQ ID NO 14
<211> LENGTH: 49
<212> TYPE: PRT
<213> ORGANISM: Artificial Sequence
<220> FEATURE:
<223> OTHER INFORMATION: Synthetic Construct

<400> SEQUENCE: 14

Arg Leu Leu Leu Leu Cys Leu Leu Arg Leu Leu Leu Leu Cys Leu
1               5                   10                  15

Leu Leu Arg Leu Leu Leu Leu Cys Leu Leu Leu Arg Asp Leu Leu
            20                  25                  30

Asp Leu Leu Leu Asp Leu Leu Leu Asp Leu Leu Leu Asp Leu Leu Leu
        35                  40                  45
```

-continued

Asp

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Leu Leu Glu Lys Leu Leu Gln Trp Lys
1               5